United States Patent [19]
Austin, Jr. et al.

[11] Patent Number: 5,201,899
[45] Date of Patent: Apr. 13, 1993

[54] CONTROL SYSTEM FOR DENTAL HANDPIECES

[75] Inventors: George K. Austin, Jr.; Paul D. Sturges, both of Newberg; Sandor Johannes, West Linn, all of Oreg.

[73] Assignee: A-DEC, Inc., Newberg, Oreg.

[21] Appl. No.: 808,946

[22] Filed: Dec. 13, 1991

Related U.S. Application Data

[63] Continuation of Ser. No. 722,669, Jun. 28, 1991, abandoned.

[51] Int. Cl.$^5$ ............................................. A61C 1/02
[52] U.S. Cl. ............................................. 433/98; 433/92
[58] Field of Search .................. 433/92, 28, 29, 98, 433/100

[56] References Cited

U.S. PATENT DOCUMENTS

| Re. 28,649 | 12/1975 | Austin, Jr. | 433/98 |
|---|---|---|---|
| 3,513,876 | 5/1970 | Tarbox | 137/596 |
| 3,918,161 | 11/1975 | Morgan et al. | 433/98 |
| 4,145,813 | 3/1979 | Hall | 433/98 |
| 4,151,647 | 5/1979 | Saupe et al. | 433/98 |
| 4,171,572 | 10/1979 | Nash | 433/29 |
| 4,173,827 | 11/1979 | Austin, Jr. | 433/98 |
| 4,188,976 | 2/1980 | Austin, Jr. | 433/28 |
| 4,230,143 | 10/1980 | Dettmann et al. | 433/98 |
| 4,459,106 | 7/1984 | Peralta et al. | 433/28 |
| 4,676,750 | 6/1987 | Mason | 433/28 |
| 4,944,676 | 7/1990 | Hu | 433/98 |

FOREIGN PATENT DOCUMENTS

| 1529130 | 10/1978 | United Kingdom . |
|---|---|---|
| 1178139A | 2/1987 | United Kingdom . |

Primary Examiner—John J. Wilson
Attorney, Agent, or Firm—Klarquist, Sparkman, Campbell, Leigh & Whinston

[57] ABSTRACT

Control system for multiple handpieces and associated devices includes a plurality of module control blocks secured in an assembly with a manifold that receives and distributes fluids to the blocks. Blocks contain cartridge valves, each removable through a single face of the control blocks for ease of access. The control blocks are adapted for attachment of auxiliary control devices. Flow control devices in the blocks are controlled by lifting of handpieces from hangers and/or by foot operated controls.

15 Claims, 14 Drawing Sheets

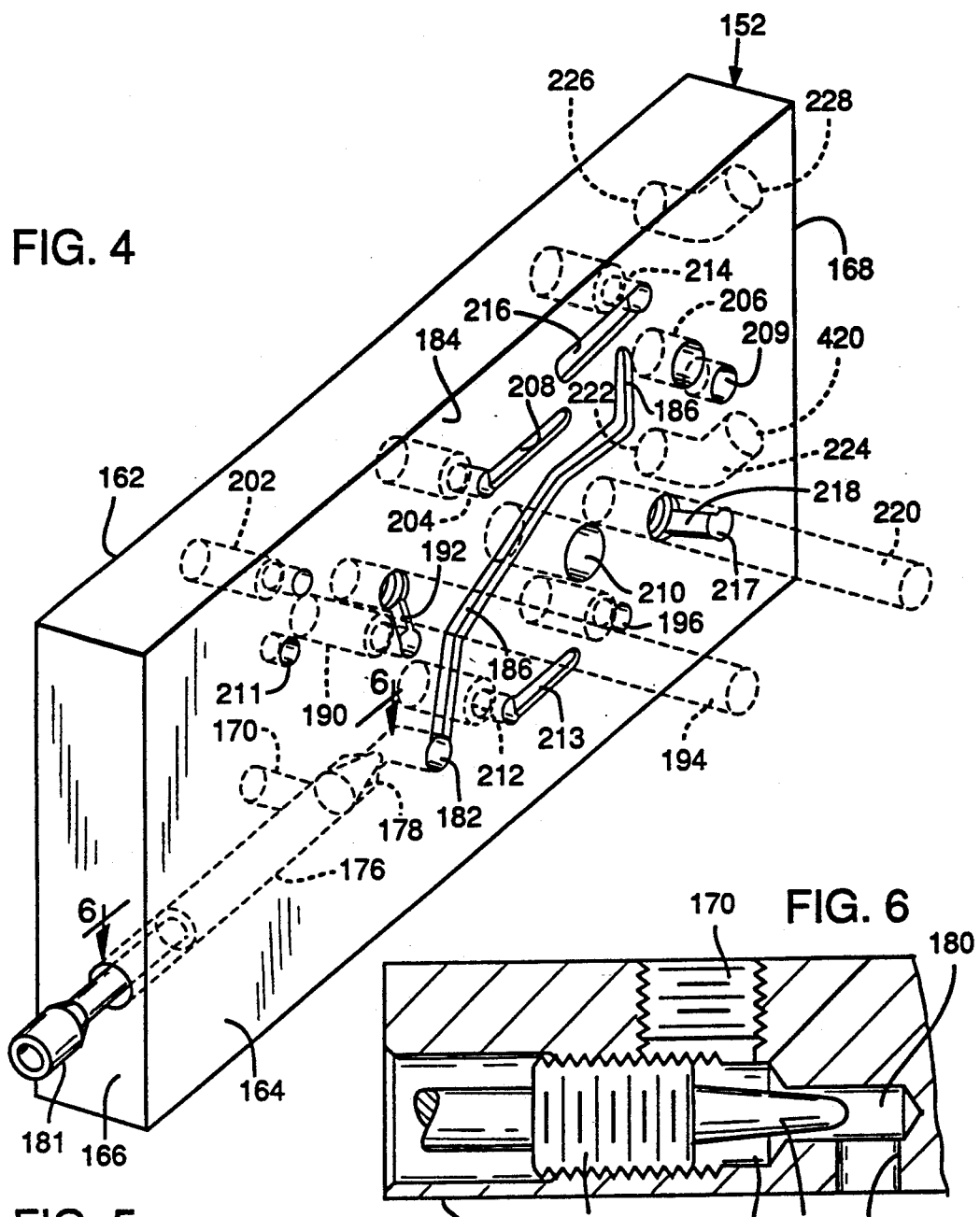
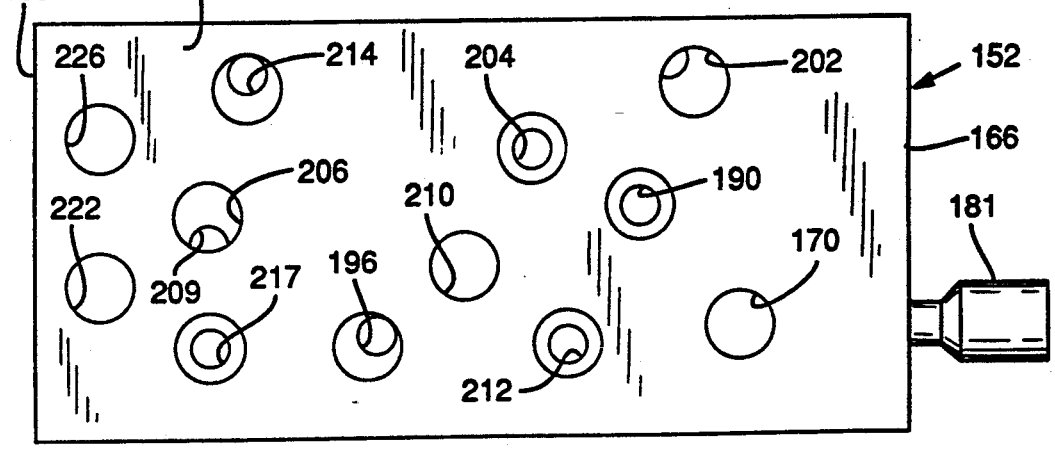

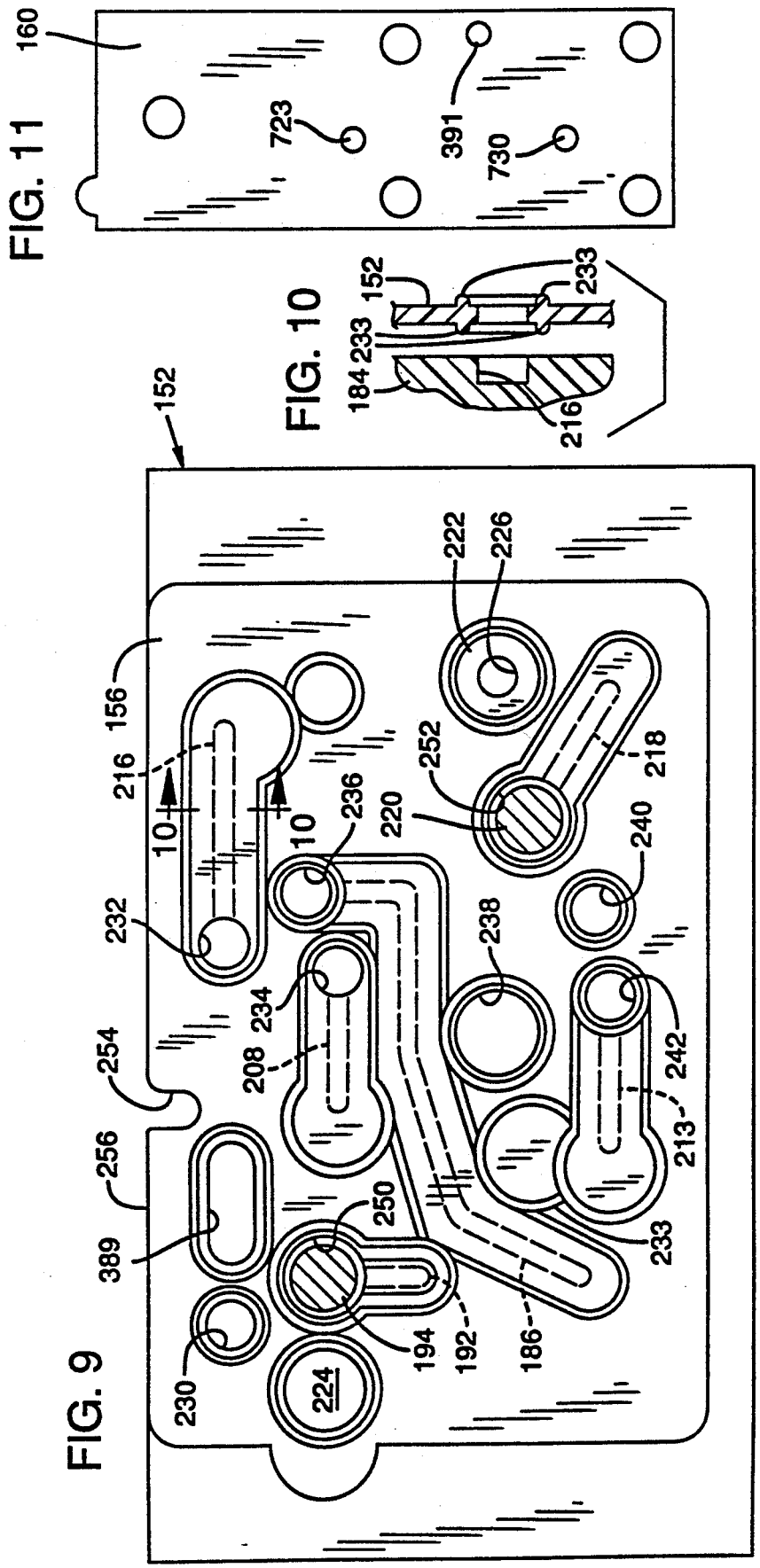

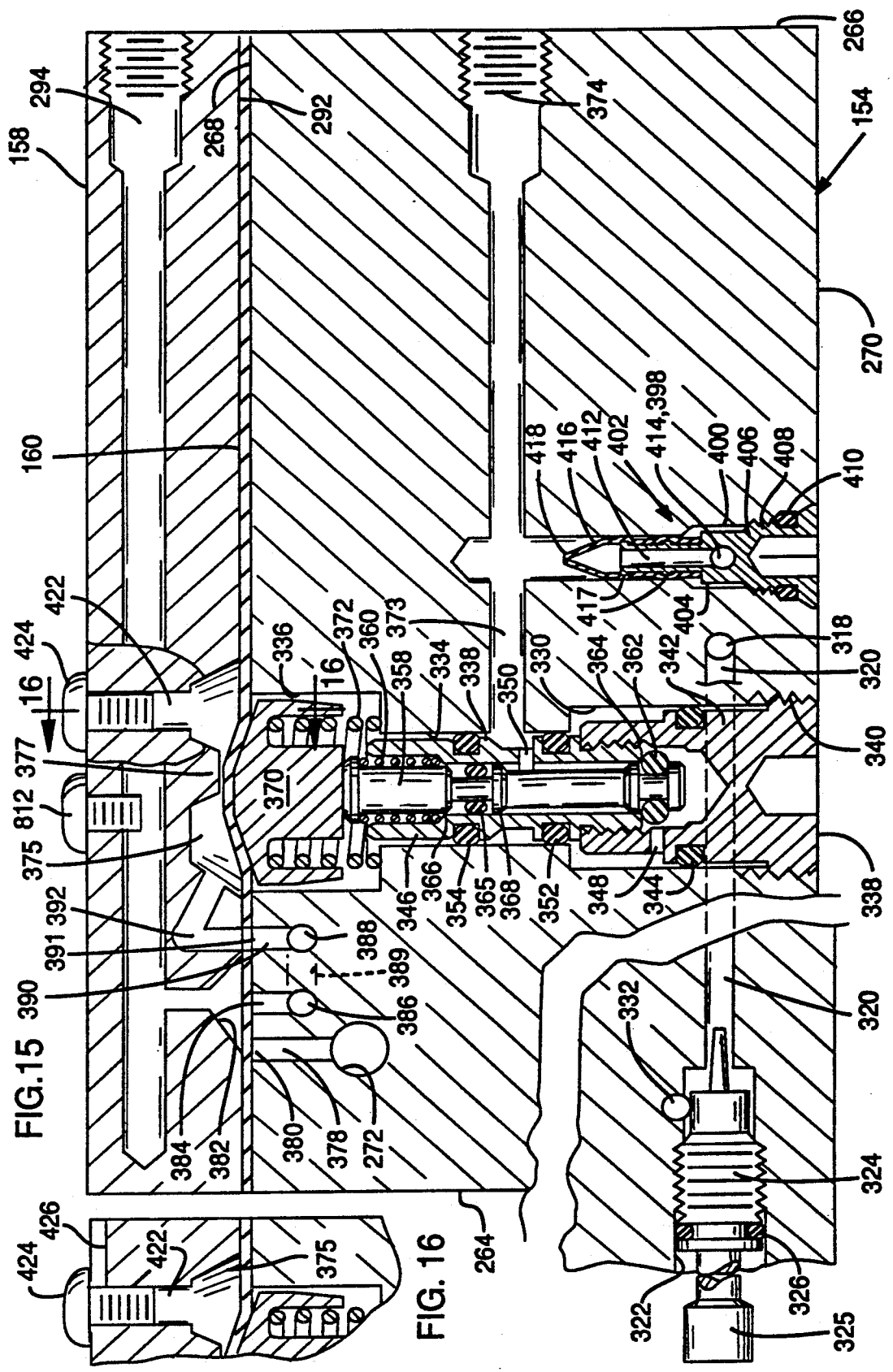

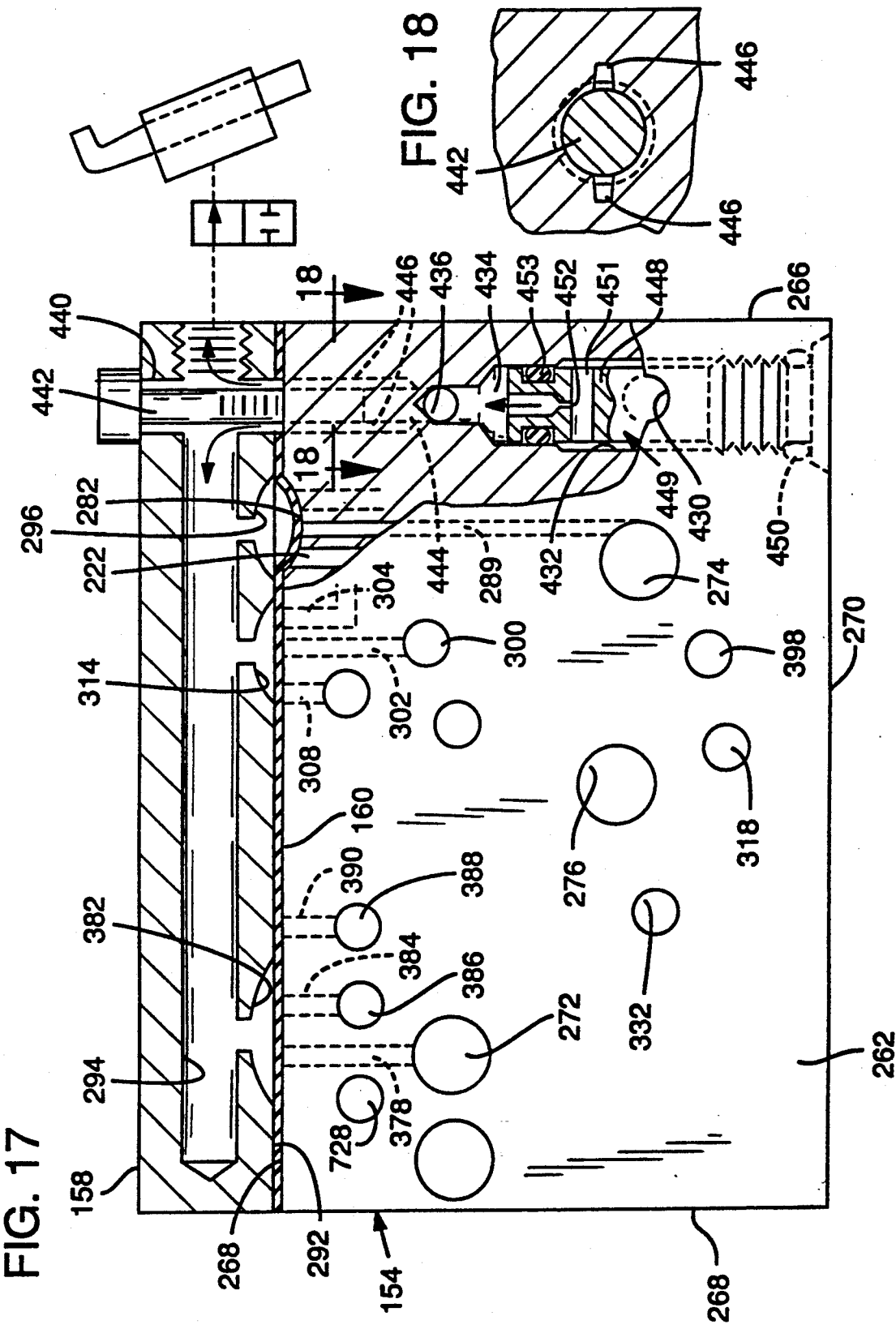

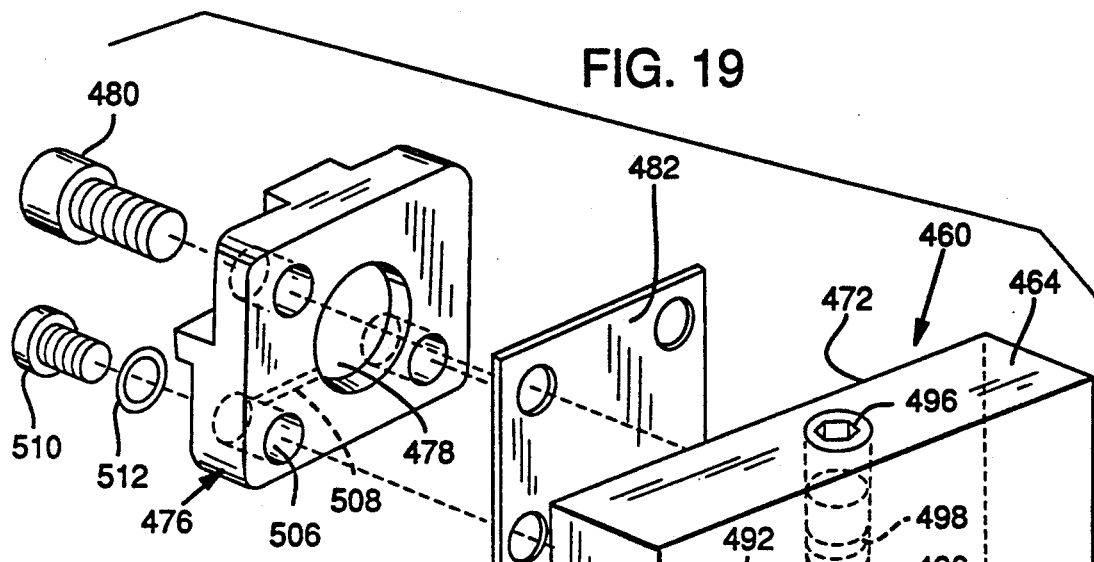
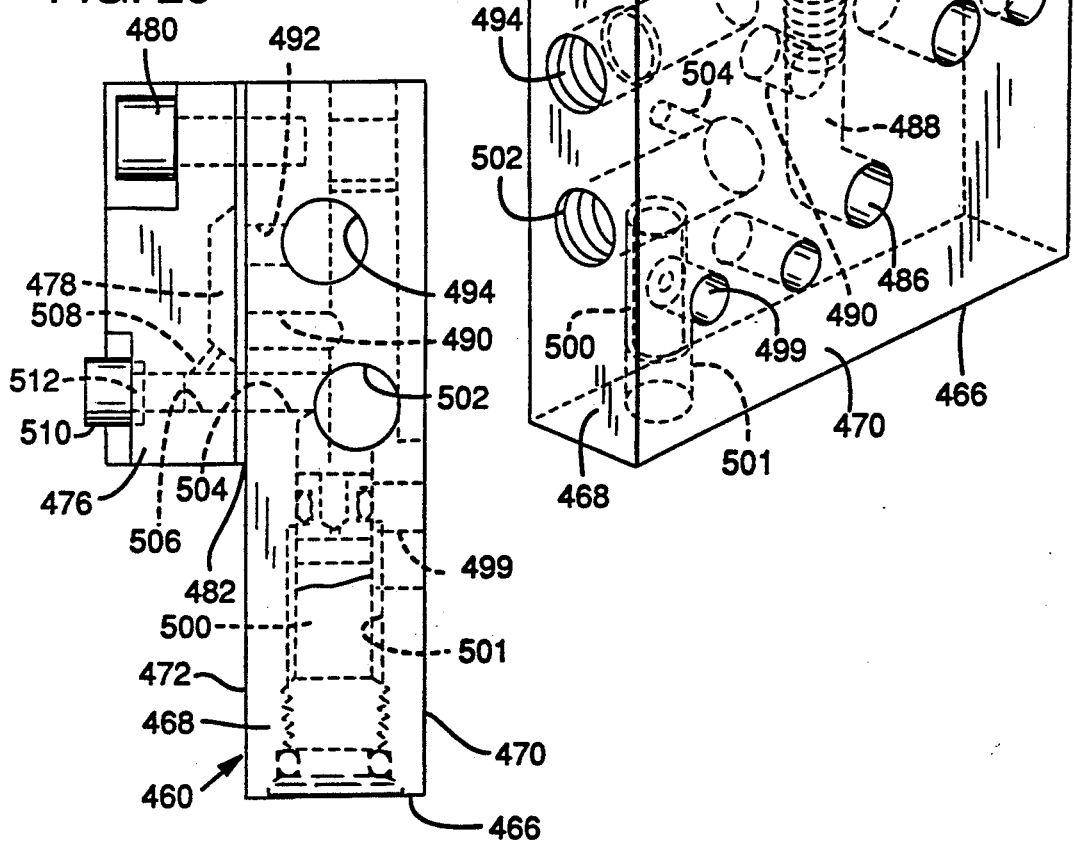

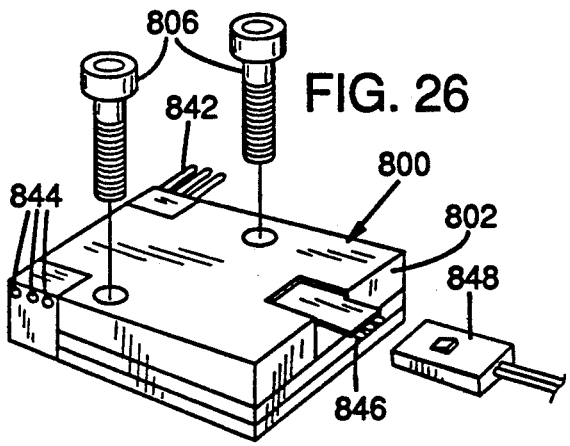
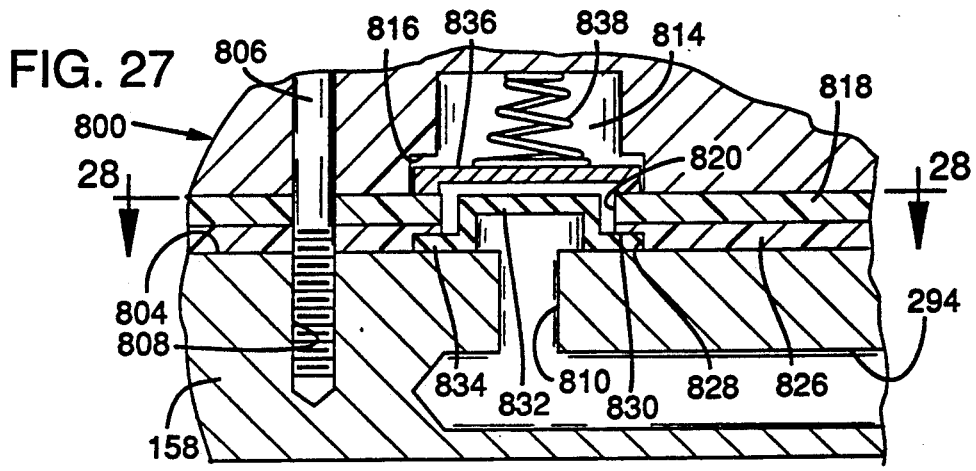
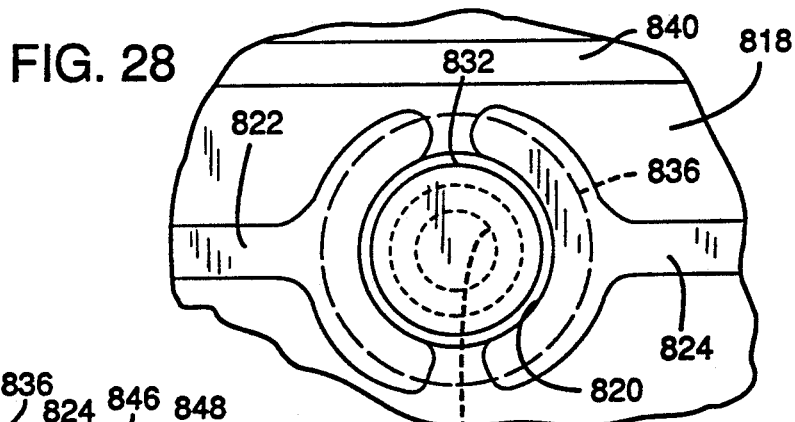
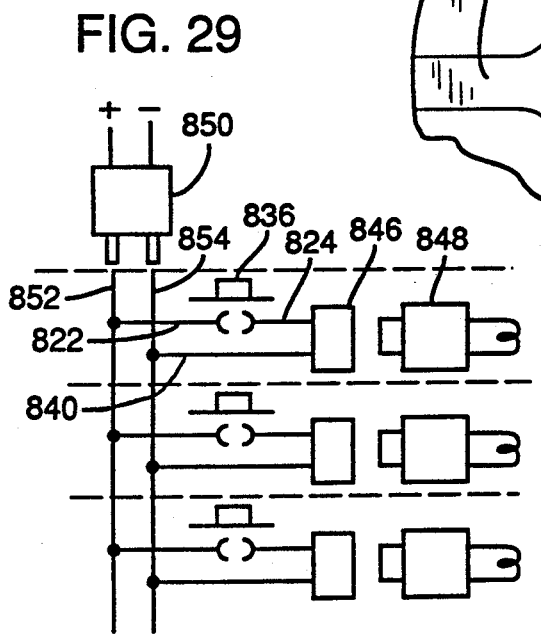

CONTROL SYSTEM FOR DENTAL HANDPIECES

This application is a continuation of application Ser. No. 722,669, filed on Jun. 28, 1991, now abandoned.

BRIEF SUMMARY OF THE INVENTION

The present invention relates to an improved system for controlling the flow of air and water to a multiple number of dental handpieces.

The present invention relates particularly to improvements in systems similar to those shown in prior U.S. patents issued to George K. Austin, Jr., one of the inventors herein, namely, U.S. Pat. Nos. RE 28,649, 4,173,827 and 4,188,976.

Control systems made in accordance with the aforesaid patents have worked admirably. The present system was devised to provide some additional advantageous features.

It is an object of the invention to provide a dental control system wherein cartridge type valves used therein may be easily and quickly removed for servicing or replacement.

Another object is to provide a basic control system to which additional control elements may be easily attached to control additional dental accessories.

Still another object is to provide a control system for controlling air and water flow to dental handpieces and other accessories wherein all fluids are introduced through a single manifold.

These and other objects and advantages of the invention will become apparent hereinafter.

BRIEF DESCRIPTION OF THE DRAWINGS

FIG. 4 is a perspective view of the manifold block of the assembly of FIG. 3;

FIG. 5 is a view of the front face of the manifold block of FIG. 4;

FIG. 6 is an enlarged sectional view taken along line 6—6 of FIG. 4;

FIG. 9 is a plan view of the gasket positioned between the manifold block and the control block showing the same positioned on the face of the manifold block;

FIG. 10 is an enlarged sectional view taken along line 10—10 of FIG. 9;

FIG. 11 is a plan view of the diaphragm which is positioned between the control block and the cap therefor;

FIG. 15 is a semi-schematic view of the path of water coolant through the control block, partially broken away to illustrate details thereof;

FIG. 16 is a cross-sectional view taken along line 16—16 of FIG. 15;

FIG. 17 is a semi-schematic view of the path of the air flow for the hold back air, i.e., the air which prevents flow of fluid through a control block;

FIG. 18 is an enlarged sectional view taken along line 18—18 of FIG. 17;

FIG. 19 is an exploded view of the elements of a modification of the apparatus of the invention to control flow of air to a tooth dryer;

FIG. 20 is a semi-schematic view of the elements of FIG. 19 in assembled condition;

FIG. 26 is a perspective view of a switch device for controlling a circuit for a fiber optic light source within a handpiece;

FIG. 27 is an enlarged fragmentary cross sectional view of the switch device of FIG. 26 and a portion of the control cap showing the device in mounted position;

FIG. 28 is a sectional view taken along line 28—28 of FIG. 27; and

FIG. 29 is a schematic of the electrical circuit for a plurality of the switch devices.

DETAILED DESCRIPTION OF THE INVENTION

Figure 1:
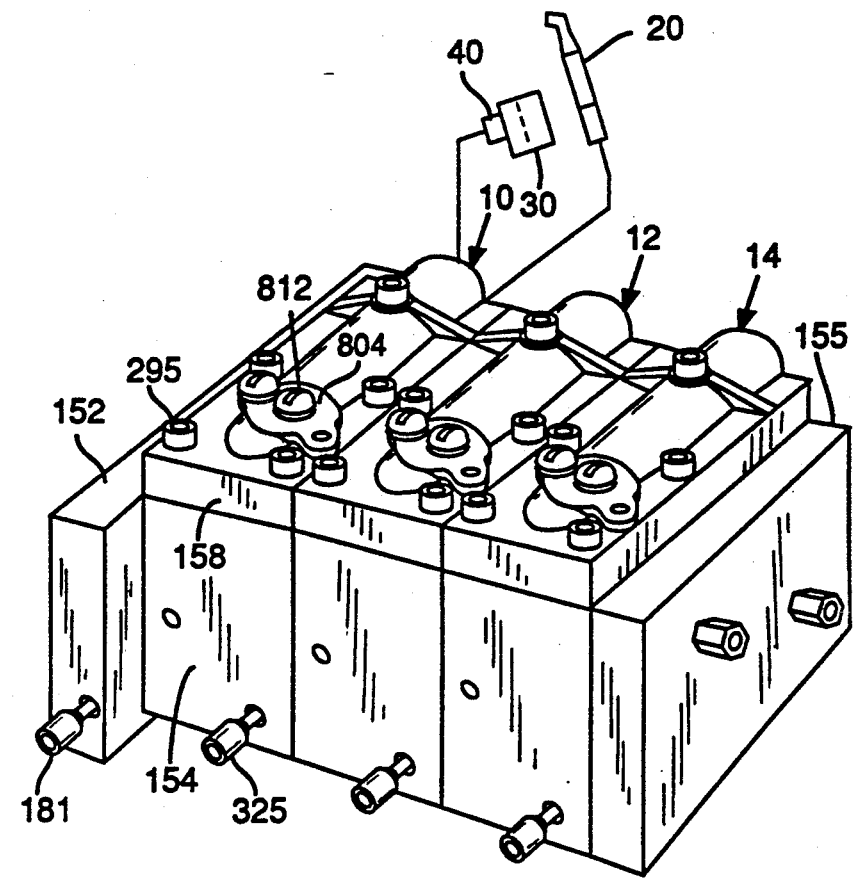
FIG. 1 is a perspective semi-schematic view of an apparatus incorporating the dental control system of the invention.
Figure 2:
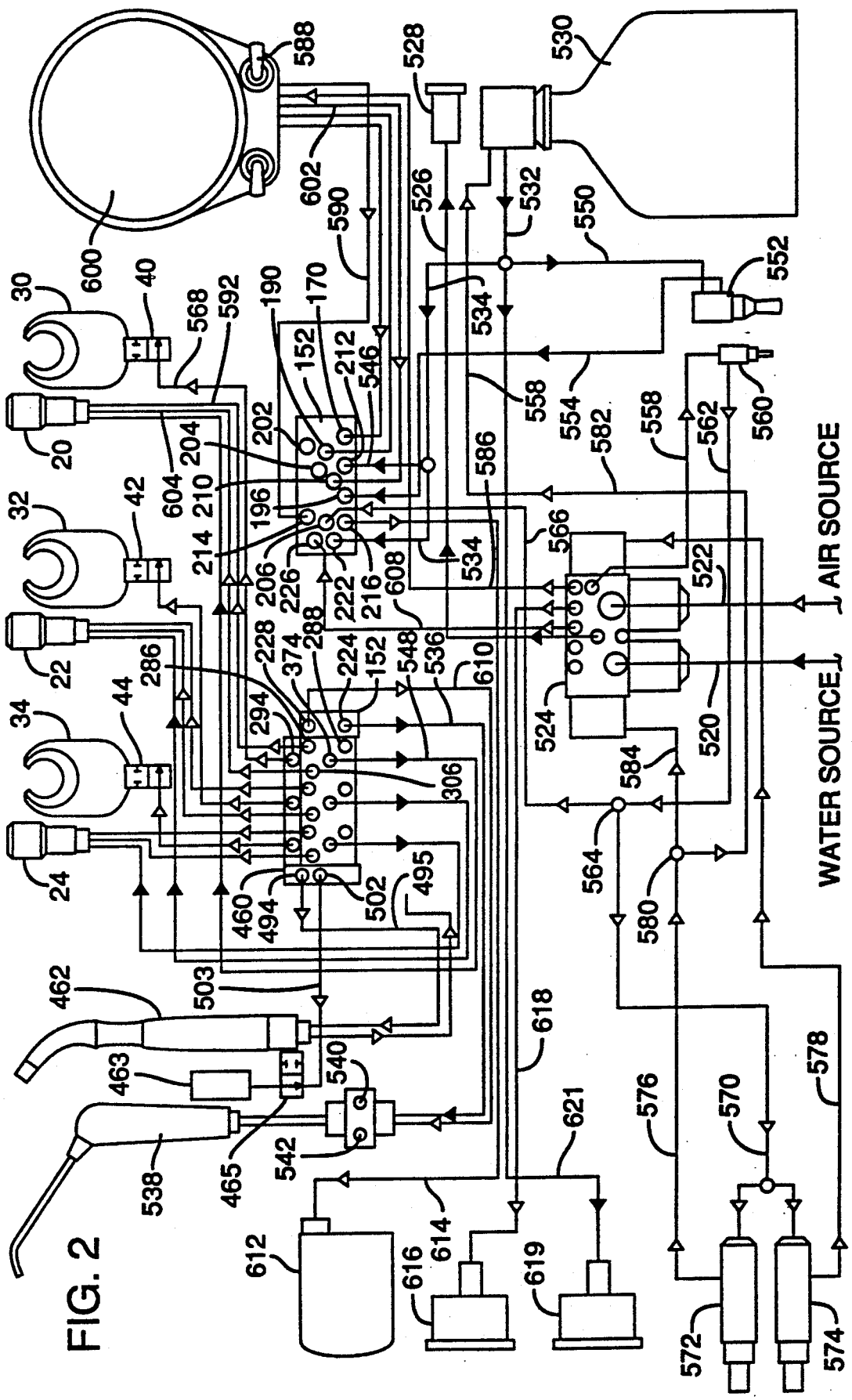
FIG. 2 is a flow diagram of the fluid circuitry of the control system of the invention.

With reference first to FIGS. 1 and 2, similarly to the systems described in earlier patents referred to above, the subject system includes a plurality of valve units 10, 12 and 14, one for each of dental handpieces 20, 22, 24, respectively. The handpieces, when not in use, are adapted to be seated in hangers 30, 32, 34, respectively. In the first to be described embodiment of the invention, lifting of a handpiece actuates a valve unit to pass air and/or water to a handpiece, while placement of a handpiece in a hanger cuts off such flow. The handpieces and hangers are connected through suitable fluid conveying tubing to the valve units in a manner to be described.

Control Units

In the illustrated embodiment, the control units 10, 12, 14 are constructed identically and are such that they may be positioned side-by-side as indicated in FIG. 1, between a manifold block 152 and an opposite end block 155, together with additional control units corresponding in total to the number of handpieces that the dentist desires to have available to him. The control unit 10 will be described in detail. It will be apparent that if special controls are desired, one or more of the units could be modified.

The control unit 10 is positioned adjacent the manifold block 152, and comprises a distribution or control block 154 and a diaphragm holddown block or cap 158. A gasket 156 (see FIGS. 9 and 10) is positioned between the manifold 152 and the control block 154. A elastomeric diaphragm 160 (see FIG. 11) is positioned between the cap 158 and the adjacent top surface of the control block 154. An orientation nib 161 is formed on one edge thereof and is aligned with a similar nib 163 on the cap 158.

Referring to FIGS. 4 through 6, the manifold block 152, is provided with an opposite pair of parallel side faces 162, 164 and opposite end faces 166, 168, the gasket 156 being engaged against the face 164. The manifold block 152 has a number of passages therethrough which are counterbored and tapped from the face 162 thereof to receive cooperatively threaded barbs to which fluid conveying lines may be connected in a conventional manner. Starting with the air coolant passage, air coolant is directed through an opening 170 in the face 162 into a valve chamber 174 in which is threadedly mounted a valve 176 having a tapered nose 178 (see FIG. 6) that is retractable into and out of the chamber outlet 180 to control the volume of air which flows out of the outlet 180. A handle 181 projects from the face 166 for positioning the valve 176. The outlet 180 has a passageway 182 leading to the face 164 of the block 152. A groove 186 in the face 164 extends from the outlet 182 across the face, as best seen in FIG. 4 and of which more will be said subsequently.

The manifold block 152 is also provided with an opening 190 in the face 162 for the passage of a signal of pressurized air to open the valve controlling flow of water coolant. A passage for the signal air is provided in the form of a groove 192, leading from the passageway 190 to an adjacent clamping bolt 194 which is secured at one end in the manifold and extends through the control blocks 154. The openings for the bolt 194 through the gasket 156 and control blocks 154 are large enough to permit the signal air to flow around the clamping bolt 194, as will be described hereinafter.

A through passageway 196 for flushing water is also provided through the manifold block 152.

Passage for conveying holdback air, that is air designed to cut-off flow of fluid through the control blocks, is provided by three passageways, namely, passageways 202, 204 and 206. Passageway 204 opens into a groove 208 formed in face 164 of the block 152. Passageway 206 opens into a gasket boss receiving opening 209 in the manifold face 164. Another boss receiving opening 211 is positioned towards the opposite end of the block.

A passageway 210 through the block is provided for drive air.

Water for injection into the oral cavity is conveyed through a passageway 212 to a groove 213 formed in the block face 164.

Air for the chip blowing is conveyed through a passageway 214 which leads to a groove 216 in the block face 164.

A passageway for connection to an air gauge line is provided at 217 which has a groove 218 leading to connecting bolt 220.

Means for connecting air and water to a syringe is also provided in the manifold. The water connection means includes a threaded barb receiving opening 222 in the face 162 which is intercepted by a threaded barb receiving opening 224 in the adjacent end face 168. The air connection means comprises a threaded barb receiving opening 226 in the face 162 which is intercepted by a similarly threaded opening 228 in the adjacent end face 168.

Referring to FIGS. 9 and 10, the gasket 156 is provided with suitable openings so that fluids may be conveyed directly through the gasket to the control block 154 from the various passageways or from the groove ends of 186, 192, 208, 213, 216, and 218 which are formed in the face of the manifold block. However, the grooves 192, 218, are closed by the gasket so as to cause the air flowing thereinto to be conveyed to the large apertures 250, 252 surrounding the respective connecting bolts 194, 220.

To facilitate correct positioning of the gasket on the manifold it is formed with a pair of bosses 222, 224 projecting from each of its opposite faces and which are adapted to fit within the openings 209, 211, respectively, in the manifold face 164, see FIG. 4. The boss 222 is formed with a passageway 226 extending therethrough. The gasket also is provided with an opening 230 in alignment with the passage 202 and an opening 232 in alignment with the end of the milled slot 216. The slot 216 and the other slots in the manifold block face 164 are shown in dotted lines in FIG. 9. To assure a tight seal around each opening and along each slot, the gasket 156 is provided with ribs such as the ribs (FIG. 9) 233 (see FIG. 10), encircling each opening and/or slot in the face 164. Also as shown in FIG. 10, the opposite faces of the gasket are mirror images in that opposite ribs are on the face thereof opposite the face engaging the manifold block 152. The gasket 156 is further provided with openings 234, 236 in alignment with the ends of the slots 208, 186, respectively. An opening 238 is provided in alignment with the passage 210 and a further opening 240 is provided in alignment with the passage 196. An opening 242 is provided at the end of the groove 213.

Openings 250, 252, FIG. 9, are provided for receiving the clamping bolts 194, 220, respectively. These openings are of a diameter greater than the diameter of the through bolts so that fluid may pass through the gasket and into the passageway around the through bolts 194, 220, defined in the control blocks 154, for purposes to be described hereinafter. The gasket 156 is also provided with a small notch 254 opening through its upper edge 256 for a purpose to be described hereinafter. The gasket 156 is also mounted between each of the control blocks 154 for the valve units 10, 12 and 14, the openings between the blocks and those in th basket being cooperatively oriented.

Control Block Construction

The distribution or control blocks 154 of the valve units 10, 12, 14 are constructed identically, one to another and only the construction of the control block next adjacent the manifold block 152 will be described in detail.

Figure 7:
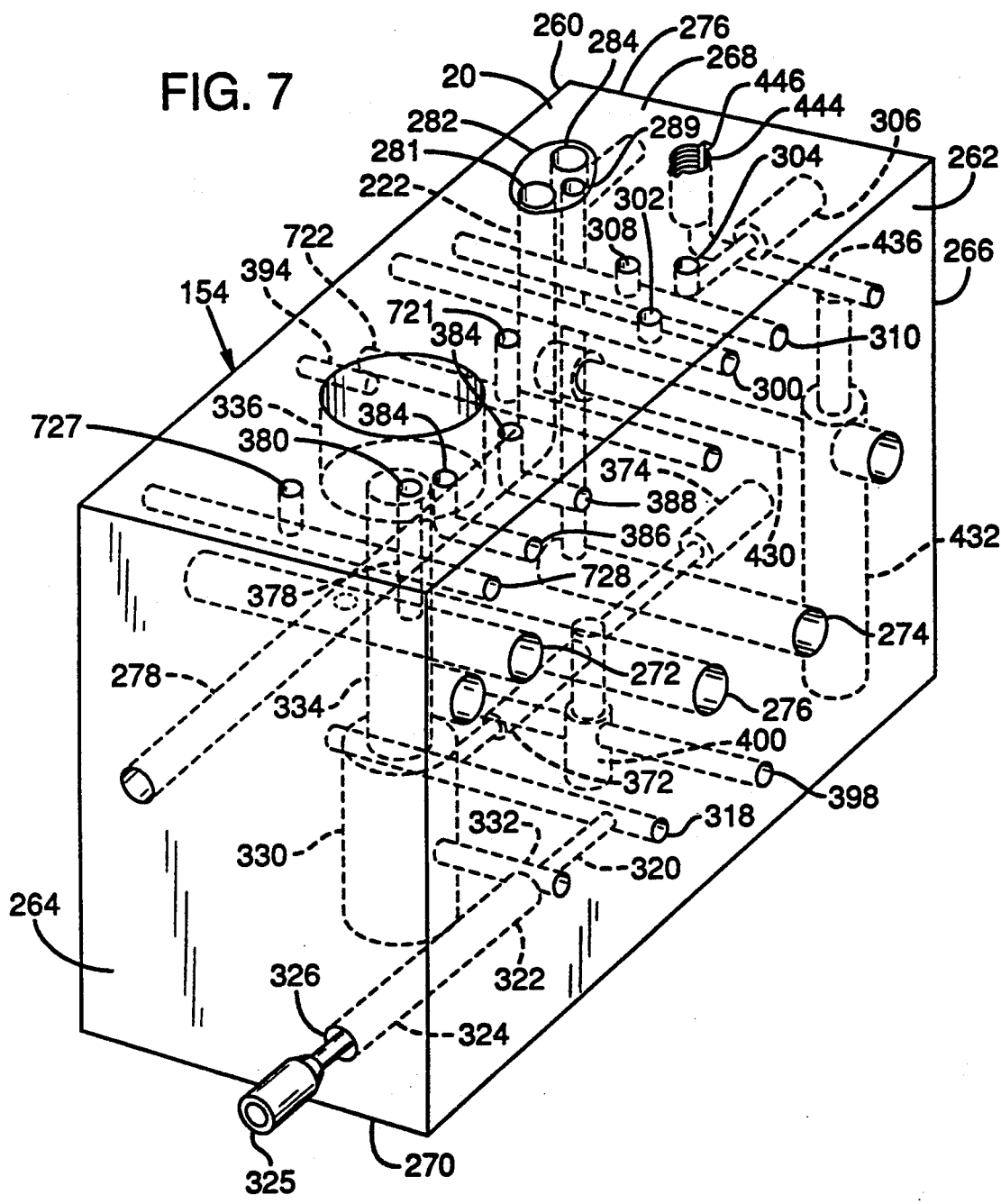
FIG. 7 is a perspective view of the control block of FIG. 3 illustrating the fluid paths therethrough.
Figure 8:
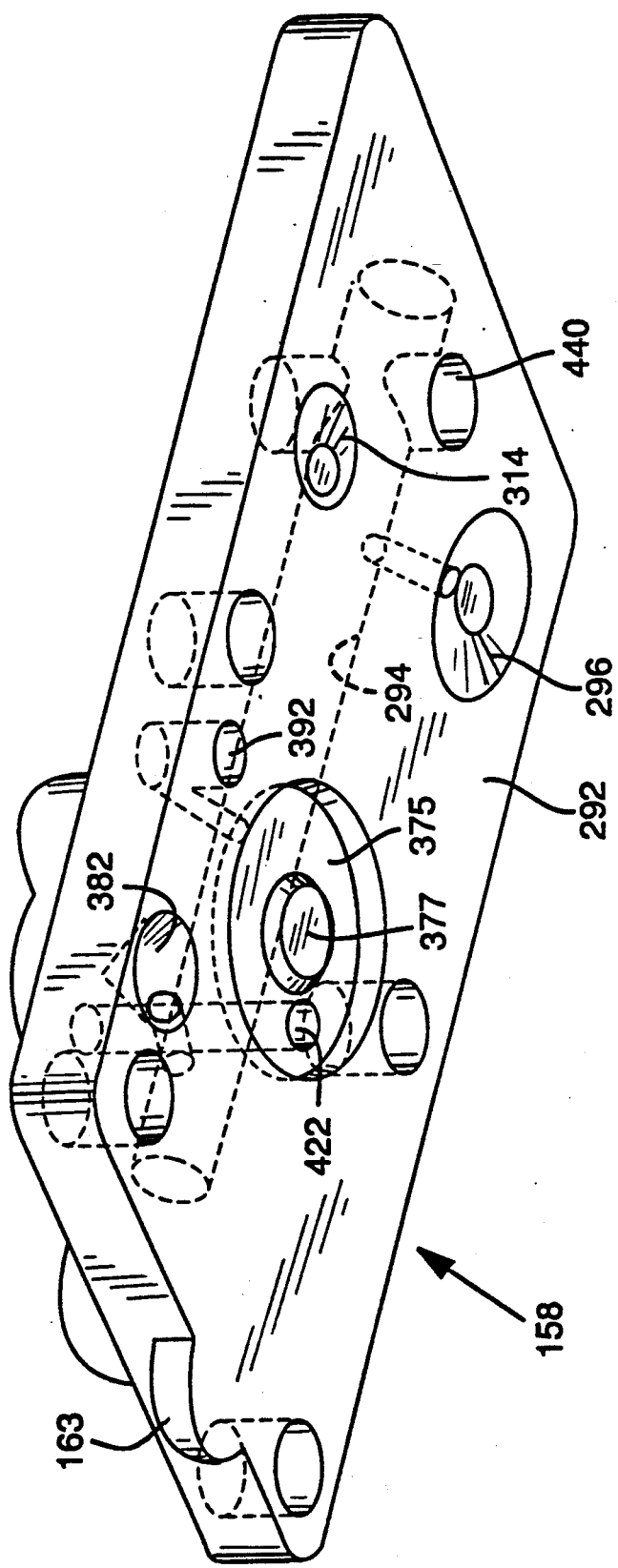
FIG. 8 is a bottom perspective view of the control block cap of FIG. 3 illustrating the fluid paths therethrough.
Figure 12:
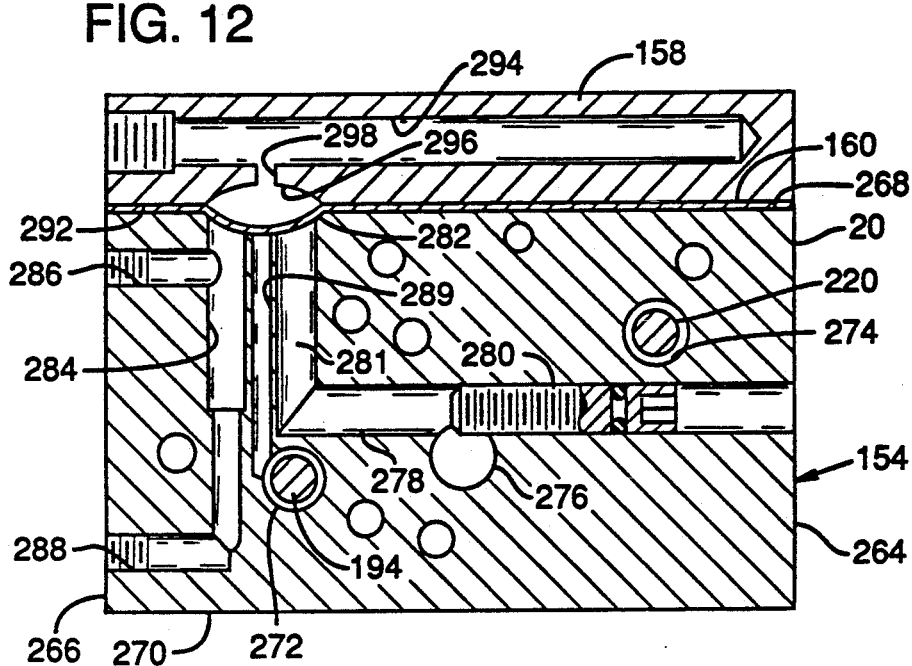
FIG. 12 is a semi-schematic view of the path of drive air flow through the control block and associated cap.
Figure 14:
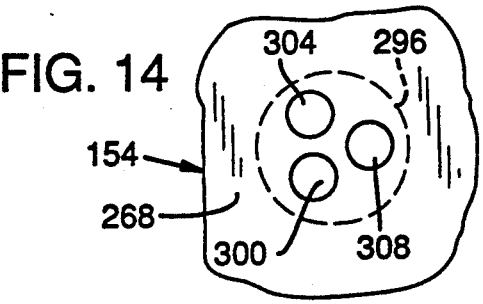
FIG. 14 is a cross-section taken along line 14—14 of FIG. 13 showing the position of the ports in the control block relative to the cap recess thereabove.

Referring to FIG. 7, the block 154 is of rectangular configuration and has a pair of parallel opposite side faces 260, 262; a pair of opposite parallel end faces 264, 266; a top face 268, and a bottom face 270. The block 152 is provided with a side-to-side pair of through openings 272, 274 for receiving the through bolts 194, 220, see FIG. 3. As mentioned earlier, these openings are of larger diameter than the through bolts so that air may flow through the block around each of the bolts. A drive air passage 276 is provided in alignment with the passage 210 in the manifold 152. The passage 276 intercepts a passage 278 drilled from the end face 264 of the control block, see FIG. 12. FIG. 12, is a semi-schematic view of the drive air circuitry within a control block 154 and the associated cap 158. The passage 278 is threaded to receive an adjustment screw 280 that may be adjusted from the face 264 to vary the size of the opening from the passage 276 into the passage 278. Passage 278 has a leg 281 which extends upwardly and opens into one side of a concave depression 282 formed in the top face 268 of the block 154. Also opening into the depression 282 is a passage 284 that extends vertically downwardly first intercepting a passage 286 drilled from the end face 266. The passage 286 is threaded to receive a cooperatively threaded barb (not shown) for connecting tubing leading to the handpiece 20 to be controlled by the control block 154. The passage 284 continues downwardly to a further passage 288 drilled from the face 266 and threaded to receive a barb.

Also connecting with the depression 282 is a passageway 289 which communicates with the fastener opening 274.

Figure 3:
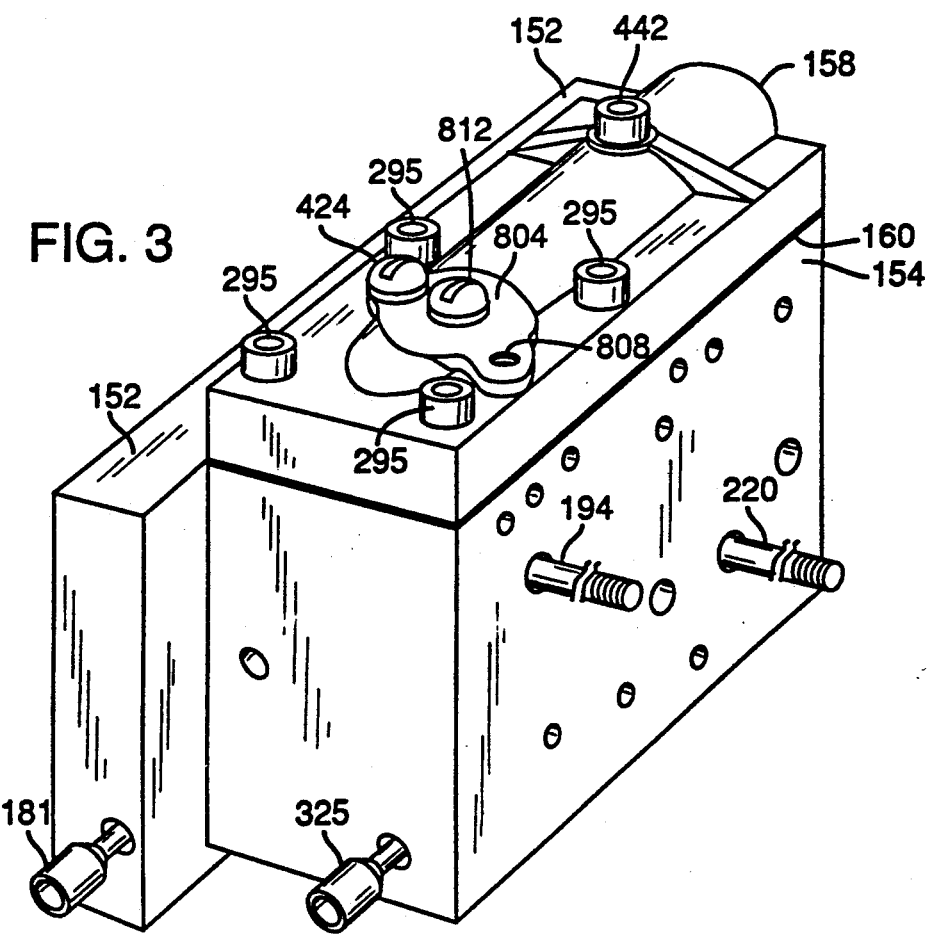
FIG. 3 is an enlarged perspective view of the assembly of a manifold block, control block and cap therefor constructed in accordance with the invention.

Positioned across the top surface 268 of the block 154 is the diaphragm 160 which is clamped between the top face 268 and the bottom surface 292 of the control block cap 158 which is secured to the control block 154 by a plurality of fastening screws 295 and 442, as shown in FIG. 3.

The cap 158 is provided with a longitudinally extending passageway 294, threaded at one end to receive a barb adapted to be connected to a tubing which in turn is connected to the valve 40 in the hanger 30. Formed in the bottom face 292 of the cap 158 opposite the depression 282 in the control block is a cavity 296 which is connected by a passage 298 to the passageway 294. When the handpiece 20 is in its hanger 30, air under pressure is passed, by means to be described, to the passageway 294, depressing the diaphragm 160 into the depression 282 to cut off air flow between the passageway 281 and the passageways 284 and 289. When the handpiece 20 is removed from the hanger 30, the valve therein opens to bleed air from the passageway 294 allowing drive air to enter through the passage 278, 281 into the depression 282 elevating the diaphragm 160 and allowing air to flow into the passageways 284, 286 and thence to the handpiece 20 to drive the same.

The recess 282 is provided in the face 268 to facilitate the provision of a passageway between the passageways 281, 284 of minimum restriction. A dental handpiece drive turbine requires a large flow of air and use of the recess 282 rather than simply bringing the openings simply to the flat face as is done in the other air controlling systems in the block.

Figure 13:
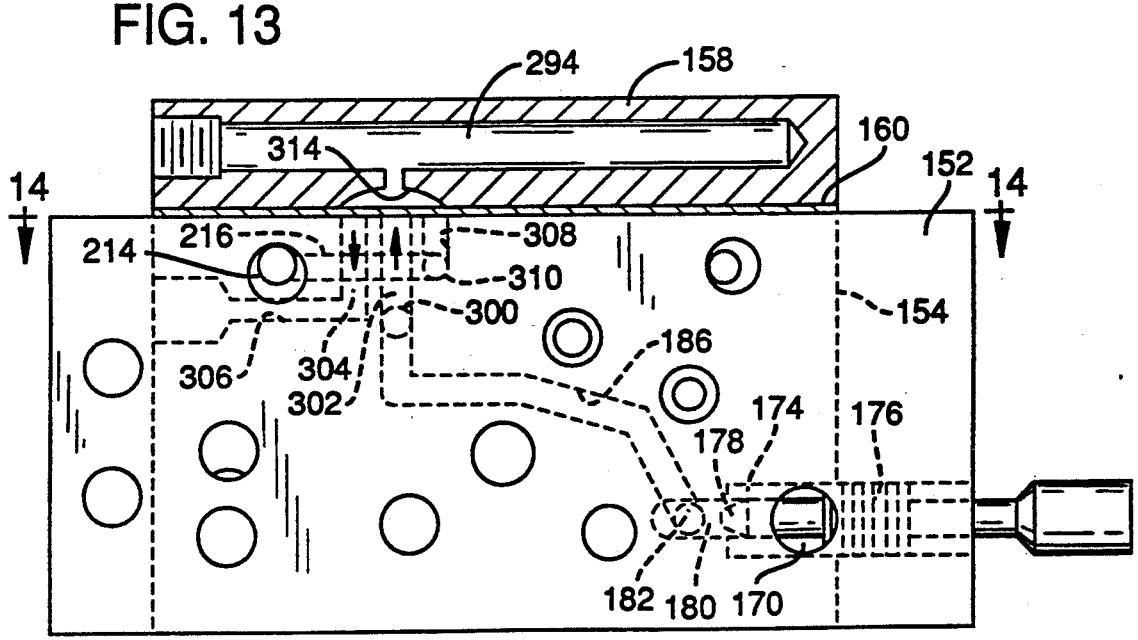
FIG. 13 is a semi-schematic view of the path of air coolant flow through the manifold and control block.

With reference next particularly to FIGS. 4, 7, and 13, the flow path for the air coolant will be described. As indicated earlier, the manifold block 152 is provided with an inlet passageway 170 for the entrance of air coolant which passes through an adjustable flow control valve 176 into a passageway 180. This in turn, leads to a groove 186 in the face 164 of the manifold block and thence to an opening 236 through the gasket 156. Concentric with the gasket opening 236 is a passageway 300 in the control block 154 which extends completely through the block 154 from the side face 260 to the side face 262. The passageway 300 is intersected by a vertically extending passageway 302 which extends to and opens onto the top face 268. Closely adjacent and parallel to the vertical passageway 302 is a further vertical passageway 304 in the block 154 which is intercepted by a horizontal passageway 306 extending inwardly from the end face 266 which is counterbored and tapped to receive a barb (not shown) for a hose connection to the air coolant receiving barb (not shown) on the handpiece. Closely adjacent the openings for the passages 302, 304, is a further vertical passageway 308 which leads to a horizontal passageway 310 which extends completely through the control block 154 from the side face 260 to the side face 262. This latter enables the handpiece to act as a chip blower as will be explained.

Formed in the cap 158 above the openings for the passages 302, 304 and 308, is a chamber 314 which communicates with the passageway 294, see FIG. 13. Thus, when the handpiece is lifted from the holder 30 and the holdback pressure is released from the chamber 294, the air coolant is allowed to flow from the passageway 302 to the passageway 306 and thence to the handpiece. When it is desired to utilize the chip clearing function, air under high pressure (about 80 psi) is directed into the passageway 214 in the manifold 152, by means described hereinafter, thence along groove 216, through gasket opening 232 into passage 310 in the control block 154, thence through passage 308 which lifts diaphragm 160 so that chip air can flow into passage 304 and thence to the handpiece.

Attention is now directed to the flow circuit for the water coolant to the handpiece with particular reference to FIGS. 4, 7, 15 and 16. Water for coolant is, by means to be described subsequently, introduced to passage 212 in the manifold. It flows from the passage 212 and groove 213 in the manifold 152 through the opening 242 in the gasket 156 to a passageway 318 which extends through the control block 154 from the face 260 to the face 262 thereof. Intercepting the passageway 318 is a passageway 320, see FIG. 7, which leads to an internally threaded valve chamber 322 which receives a cooperatively threaded valve stem 324 having a tapered nose extending into the passageway 320. By advancing or retracting the valve stem 324 by means of the external handle 325, the flow of fluid through the passage 320 into the chamber 322 can be controlled. An o-ring 326 is mounted on the valve stem 324 for engagement with the wall of the chamber 322 to prevent escape of coolant water past the valve stem.

Formed in the block 154 from the bottom face 270 thereof, is a large chamber 330. Communication between the upper end of the chamber 330 and the valve chamber 322 is provided by a passage 332 drilled from the face 262 to intercept the upper portion of the valve chamber 322 and the chamber 330, see FIG. 16. The passage 322 is sealed at the face 262 in the assembled units by the presence of the rib 233 formed on the gasket 156 and encircling the passage 332. Extending upwardly from the chamber 330 is a bore 334 which opens into a counterbored aperture 336 extending downwardly from the top face 268 of the block 154. Mounted in the valve chamber 330 and bore 334 is a poppet-type cartridge valve 338. The base 342 of the valve 338 is threaded as indicated at 340 to mate with cooperative threads formed in the lower end of the valve chamber 330 so that the valve 338 may be mounted securely in place. Surrounding the base 342 of the valve body is an o-ring 344 which engages the sidewall of the chamber 330 just beneath the passage 332 so as to prevent escape of coolant water out of the lower end of the chamber 330.

The poppet valve 338 includes a hollow stem 346 which is fitted within the bore 334. The stem 346 has an entry port 348 for water entering from the chamber 330 and an exit port 350 positioned above the entry port, there being an o-ring 352 positioned around the stem between the entry port 348 and the exit port and a further sealing o-ring 354 positioned above the exit port 350. Vertically slidable within the stem 346 is a valve core 358 which is biased upwardly to a valve closing position by a spring 360. Mounted at the lower end of the core 358 is an o-ring 362 that is adapted to engage the lower shoulder 364 of the stem 346 when the valve is in closed position to prevent the entry of water upwardly along the valve core. A further o-ring 365 is mounted on the stem between two stops 366, 368 to prevent flow of water upwardly out of the stem. The o-ring 365 is positioned to be above the outlet 350 in both the open and closed position of the valve core 358. Positioned in the aperture 336 for vertical movement is a cap 370 which is biased upwardly by a spring 372. Depression of the cap 370 will cause the valve core 358 to be depressed to open a fluid path through the valve from the passage 332. When the valve 338 is opened, the water coolant can flow out of the exit opening 350 through a passageway 373 to an exit port 374 formed in the end face 266 of the block 154. The exit port 374 is threaded to receive a barb (not shown) to which tubing may be connected to conduct coolant water to the handpiece.

Formed in the cap 158 above the cap 370 is a recess 375. The recess 375 is formed with a depending boss 377 in the center thereof against which the cap 370 engages when it is in its upward position, leaving an annular recess around the periphery of the recess through which actuating air may flow when it is desired to actuate the valve 338 as will be explained. The diaphragm 160 extends across the top of the cap 370 sealing it and the aperture 336 from the recess 375. In the normal operating condition, the spring 372 has sufficient strength to bias the cap 370 to engage the boss 377.

Means are provided for actuating the valve 338 at the direction of the dentist to permit cooling water to flow to the handpiece 20. For that purpose, a control valve is provided in the foot-actuated control for the dentist. Actuation of this will cause high pressure air to flow through manifold opening 190 and groove 192 by circuitry to be described into bolt opening 272 in the control block 154. Such air is led from the passage 272 upwardly through a passage 378 to a port 380 positioned beneath a recess 382 formed in the cap 158 so that about twenty percent of the port diameter is overlapped by the cap 158. The recess 382 has a passage leading to the passageway 294. A second port 384 positioned beneath the recess 382 leads downwardly and is intersected by a passageway 386 drilled inwardly from the face 262. Adjacent the passage 386 is a parallel passageway 388 drilled in from the face 166 and which intersects a vertical passageway 390 drilled downwardly from the top face 268. The gasket between the block 154 and the next adjacent control block is formed with a slot 389 which bridges the ends of the passageways 386 and 388 to permit air to flow from the passageway 386 to passageway 388. The diaphragm 160 has an opening 391 in register with the passageway 390 which is also in alignment with a passageway 392 formed in the cap 158 and which leads to the recess 375. Thus, when air under pressure is admitted by reason of operation of the foot control by the dentist so as to flow into the manifold opening 190 and through the air circuitry just described to lift the diaphragm 160 in the recess 282, the air flows to the recess 375 over the top of the diaphragm 160 to effect depression of the cap 370 and opening of the valve 338 to permit water to flow to the handpiece. When the foot control is released to close off the control air, the pressure in the passage 294 causes the diaphragm once again to be pressed against the port 380 to close the same. It has been found that when the port 380 is partially overlapped by the cap 158 as described above, a more effective closure of the port is obtained to assure water cut off and diaphragm life is prolonged.

Means are provided to flush the handpiece water lines with clean water. Referring to the FIGS. 7 and 15, extending through the control block from the face 260 to the face 262 in line with the passageway 196 in the manifold block 152 is a passageway 398. The passageway 398 extends through a chamber 400 drilled from the bottom face 270. Mounted in the chamber 400 is a check valve 402 in the form of a duckbill valve, including a brass body 406 with an enlarged threaded end 408 to engage in cooperative threads formed in the lower end of the chamber 400. An o-ring 410 is positioned on the neck at the lower end of the valve body 406 to form a seal against escape of water from the chamber. The valve body 406 is provided with an axial opening 412 from the end opposite the threaded end, which axial opening 412 extends downwardly to an aperture 414 extending crosswise through the body so that water can flow from the chamber 400 upwardly through the upper end of the valve body. Surrounding the upper end of the valve body, which is of reduced diameter, is a tubular lower end of a flexible duckbill element 416, the upper end of which is formed so that the ends resiliently engage each other at 418 so that water can flow outwardly from the tubing 416, but not inwardly thereinto. The chamber 400 intercepts the passageway 373 whereupon by actuation of means to be described, flush water will enter the passageway 398, flow into the passageway 373 and through the handpiece connected thereto.

The recess 375 is also provided with a safety bleed-off or leak from the portion of the recess positioned above the diaphragm 160. This leak is in the form of a threaded opening 422 extending downwardly from the top of the cap 158 into the cavity 375, in which opening is contained a screw 424. The opening 422 is intercepted by a groove 426 in the top surface of the cap 158, see FIG. 16. The fit of the thread of the screw 424 in the opening 422 is such that air may leak past the screw and through the groove 426 at a relatively slow rate for a purpose to be described subsequently.

The holdback air circuit will now be described, that is, the circuitry in the control block 154 and cap 158 which maintains a control block in inactive position with the diaphragm 160 pressed downwardly to prevent fluid flow through the control block to the handpiece, with particular reference to FIGS. 4, 7 and 17. Unregulated air through the circuitry to be described is applied through passageways 206, 209 in the manifold 152 and the opening 226 through the gasket boss 222 into an air supply passageway 430 extending through the control block 154. The passageway 430 is intercepted by a bore 432 drilled from the bottom face 270, the upper end 434 of which is of reduced diameter. The reduced upper end portion is intercepted by a horizontal passageway 436 formed by drilling from the face 262 inwardly approximately to the center of the block beneath the axis of the cap passageway 294. Extending downwardly from the top of the cap 158, intersecting the axis of the opening 294, is an opening 440 for slidably receiving a bolt 442, which extends into a cooperatively threaded opening 444 in control block 154. The opening 444 intersects passageway 436, the side of the opening 444 being provided with a pair of diametrically spaced broached slots 446 (see FIG. 18) to facilitate the passage of air upwardly from the passage 444 into the passageway 294. Mounted in the bore 432 is bleed valve 448 comprising a body 449 of brass or other suitable material having an enlarged threaded lower end engaging cooperative threads in the bore 432. An o-ring 450 provides an air seal at the lower end of the body 449. The body 449 is formed with a diametric passage 451 which leads to a 0.005" bleed orifice 452 through which air may pass to an axial aperture in the upper end of the body. An o-ring 453 is positioned on the body above the passage 451 to prevent air leakage around the body. When the handpiece controlled by the control block 154 is in its holder, the air passing through the passage 430 and bleed valve 448 will apply sufficient pressure to the diaphragm in the recesses 296, 314 and 382 to close off all flow through the passages having ports beneath such recesses.

The bleed off past the screw 422 assures cut off of water flow to the handpiece 20 when it is placed in its hanger even though the foot control is inadvertently still depressed by a dentist. This might cause air to leak through port 380 and thence to the cavity 375 over the water valve. However, the leak past the screw 422 will reduce the pressure in the cavity 375 so that the spring 372 can raise the cap 370 so that the valve 338 will close.

In the basic embodiment of the invention at the end of the row of the control blocks opposite the manifold block, is positioned a close-off block 155 (see FIG. 1), which simply functions to terminate all of the through passageways in the block 14 which distribute air and water to each of the control blocks 154. A gasket 156 or other suitable gasket is positioned between the close-off end block 155 and the adjacent control block to seal all passageways.

In an alternative embodiment of the invention, the end block 155 may be replaced with a control block 460 (shown in FIGS. 19 and 20) for controlling the flow of air to a tooth dryer 462 having a holder 463 controlling a normally open valve 465 (see FIG. 2). The control block 460 has a top face 464, a bottom face 466, an end face 468, a side face 470, which nests against the adjacent handpiece control block 154 with an intervening gasket 156, and an opposite side face 472. Attached to the side face 472 is a diaphragm control cap 476 formed with a recess 478 in the face thereof adjacent the side face 472. The cap is secured to the face 472 by means of two screws 480 which thread into cooperative openings in the block 460. A flexible diaphragm 482 is interposed between the cap 476 and the control block face 472. Air to operate the tooth dryer is conveyed from the drive air passage 276 of the adjacent handpiece control block 154 via a mating passageway 486 extending inwardly from the face 470 so as to intercept a vertical passageway 488 drilled downwardly from the top face 464. The passageway 488 is intercepted by a passageway 490 which opens onto the side face 472 opposite the diaphragm depression 478 in the control cap 476. A further passageway 492 is drilled inwardly from the face 472 adjacent the passageway 490 and opposite the diaphragm recess 478. The passageway 492 intercepts a passageway 494 which opens into the end face 468 and which is internally threaded to receive a barb for connection to a hose 495 leading to the tooth dryer 497, see FIG. 2. A control valve to control the rate of flow of air to the tooth dryer is provided by means of a valve body 496 which is threaded into the passageway 488 so as to intercept the passageway 490. By varying the elevation of the valve body 496, the rate of air flow from the passageway 488 to the passageway 490 and thence to the handpiece can be controlled. The upper end of the valve body 496 is provided with a cooperative groove for receiving a sealing o-ring 498 which engages against the side wall of the passageway 488.

Formed in the block 460 from the face 470, is a passageway 499 concentric with the passageway 430 in the control block 154. The passageway 499 intercepts a vertical counterbored opening 501 formed from the bottom face 466 and in which is mounted a bleed valve 500 identical to the valve 436 described previously. Intercepting the opening 501 is a passageway 502 drilled from the face 468. The outer portion of the passageway 502 is threaded to receive a barb for connection of a hose 503 to a normally open valve in the holder 504 for the tooth dryer 462 (see FIG. 2). Drilled from the face 472 is a passageway 504 which intercepts the passageway 502 and is in line with an opening 506 extending through the cap 476. A passageway 508 extends from the opening 506 into the recess 478. The opening 506 is threaded to receive a machine screw 510 which can be tightened against a washer 512 to seal the opening 506 and prevent the escape of air outwardly of the opening 506.

When the tooth dryer 462 is in its holder 463 the valve 465 will be closed and air flowing through the valve 500 and passages 502, 504, 506 and 508 will maintain pressure in the recess 478 to press the diaphragm 482 against the control block surface 472 shutting off flow of air from opening 502. When the tooth dryer 462 is removed from its hanger, however, the valve 465 in the hanger will open to vent air from above the diaphragm 482, thus allowing air to flow to the tooth dryer 462. This may be a tooth dryer with an internal heating means, such as shown in U.S. Patent No. 4,937,246, Black et al.

Operation

The operation of the embodiment above mentioned will now be described starting with FIG. 2 which illustrates the fluid circuitry of the apparatus. Water and air are introduced through lines 520, 522, respectively, from suitable sources to a utility module 524, which contains water and air filters and distribution channels for diverting water and air to desired exit ports. After passing through the filter, the water is directed through an exit line 526 to a water outlet 528 which may be connected to various dental equipment including an outlet by means of which a water bottle 530 may be filled to supply the requirements for the operation of the handpieces in the course of a days' operation. The water contents may be supplemented by saline or other chemicals as the dentist feels necessary or desired. The water from the bottle 530 is maintained under air pressure so that it may be fed from the bottle to the system through an exit line 532 which connects to a line 534 leading to the inlet port 222 in the manifold 152, and thence to the exit port 224 therein and a tubing 536 by means of which it is conveyed to the handle of a syringe 538 having hand operated control buttons 540, 542 for air and water, respectively. Coolant water for the handpiece is introduced through conduit 534 and a conduit 546 to the inlet 212 in the manifold 152. From there it flows through the control valve 324 in the control block and thence to the outlet 374 to a connecting hose 548 to the handpiece 20.

Water for effecting flushing flows from the bottle 530 through a line 550 to a manually operated flush control valve 552, thence through a line 554 to the inlet 196 in the manifold block. From there, it flows into the control block and through the duck bill valve 402 finally emerging via the opening 374. From there it flows to from the handpiece through the hose 548. Flushing will not ordinarily occur during operation of the handpiece, but can be caused manually at the election of the dentist when the handpiece is not operating to help flush any organisms which may have entered the coolant water passages in the handpiece 20 while it is in the oral cavity.

Air from the supply 522 is passed through the utility module and an air filter therein to a master on/off valve 560 through a line 558. Air flows from the valve 560 through a line 562 to a divider 564 from which a line 566 leads to passage 206 in the manifold 152. Air flowing into the passage 206 passes through the passage 209 and through the opening 226 in the boss 222 into the air supply passageway 430 in the control block 154. From it, it passes through the bleed valve 448 and thence into the hold down passage 294 in the cap 158. So long as a handpiece is in its holder, the pressure in the passage 294 will be maintained sufficient to press the gasket 160 into engagement with the various openings, as shown in FIG. 17, to prevent flow between passages beneath the recesses 296, 314 and 382. The passageway 294 in the cap is connected to the normally opened valve 40 in the handpiece hanger 30 through a hose or tube 568. This hose and the valve 40 are of such diameter that when the valve is opened, air is exhausted at a much more rapid rate from the passage 294 than air is supplied to it through the bleed valve 448. This relieves the pressure over the diaphragm 160 so fluid can flow through the control block upon operation of the conventional control valves in the dental handpiece.

From the divider 564 air also flows through a line 570 to a pair of pressure regulators 572, 574. The regulator 572 is designed to provide exit air through a line 576 at 30 psi. The regulator 574 provides air through an exit line 578 at 80 psi. The line 576 is connected to a divider 580 to which is connected a line 582 for conveying air to the top of the water bottle 530 to maintain it under pressure so that water will be forced therefrom upon operation of a control valve by the dentist. Another line 584 conveys 30 psi from the divider 580 to the utility module 524. The 80 psi line 578 is also connected to the utility module 524.

The 80 psi air flows through the module to an output conduit 586 which leads to a chip air controlling foot-operated control valve 588 mounted in the dentist's foot control 600. When the foot control 588 is opened by the dentist, air flows through a line 590 to the manifold opening 214. From thence, it flows through the groove 216 in the face of the manifold, through the gasket opening 232 into the passage 310 in the control block 154 (see FIG. 13). Thence it flows through passage 308 and, because it is at 80 psi, which is substantially greater than the pressure above the diaphragm, it can lift the diaphragm so that air can flow into passage 304 and thence to the handpiece 20 through a line 592 from opening 286 in the control block 154.

The air for driving the turbine in the handpiece is also controlled by the foot valve 600. When it is depressed by the dentist, air flows through a valve therein through a line 602 to the manifold opening 210. If the handpiece 20 is out of the holder 30, the drive air will flow into the passage 276 of the control block past the adjusting screw 280, through the line 281, and thence upwardly into the depression 282 (see FIG. 12). Because the pressure above the diaphragm 160 has been relieved, the diaphragm will be elevated allowing air to flow downwardly in passage 284 to the outlet 286 from whence it will be conveyed to the handpiece through a line 604. If the handpiece is still in the holder 30, the pressure above the diaphragm will keep it in closed position preventing drive air flowing to the handpiece.

The syringe 538 is supplied with air from the utility module 524 via a line 608 which leads to opening 226 in the manifold. From thence it flows out of the manifold through opening 228 (see FIG. 4) and through a line 610.

The handpieces 22 and 24 and their respective hanger valves function in a similar manner.

Pressure gauges are also supplied to measure the pressure. A gauge 612 for measuring the drive air pressure is connected by a line 614 to opening 216 in the manifold block, which it will be recalled communicates via a groove 218 to the connecting bolt opening 274 which in turn communicates with the recess 282 through a passageway 289, as shown in FIG. 12. Air pressure (80 psi) at the utility module is measured through an air pressure gauge 616 connected via line 618 thereto. The 30 psi pressure over the water in the source bottle 530 is measured by a gauge 619 connected by a line 621 and line 532 to the top of the bottle.

Modification

The apparatus of the invention is subject to certain modifications which will now be described. As will be evident, the foregoing circuitry above described will not function to prevent operation of more than one handpiece at a time. That is, if the handpiece 22 is removed from its hanger at the same time as the handpiece 20, each can operate. In one modification of the invention, the apparatus is modified so that when the first of the handpieces 20, 22 or 24 is removed from its hanger, it is rendered operative, but none of the others may operate so long as the first handpiece remains removed from its hanger. When the first removed handpiece is returned to its hanger, it is rendered inoperative and any of the other handpieces can be similarly rendered operative by removing it from its hanger. In this modification of the invention, each of the control caps 158 are replaced by control caps 620 which are constructed identically and constitute valves indicated at 660, 662 and 664 in FIG. 21.

Figure 22:
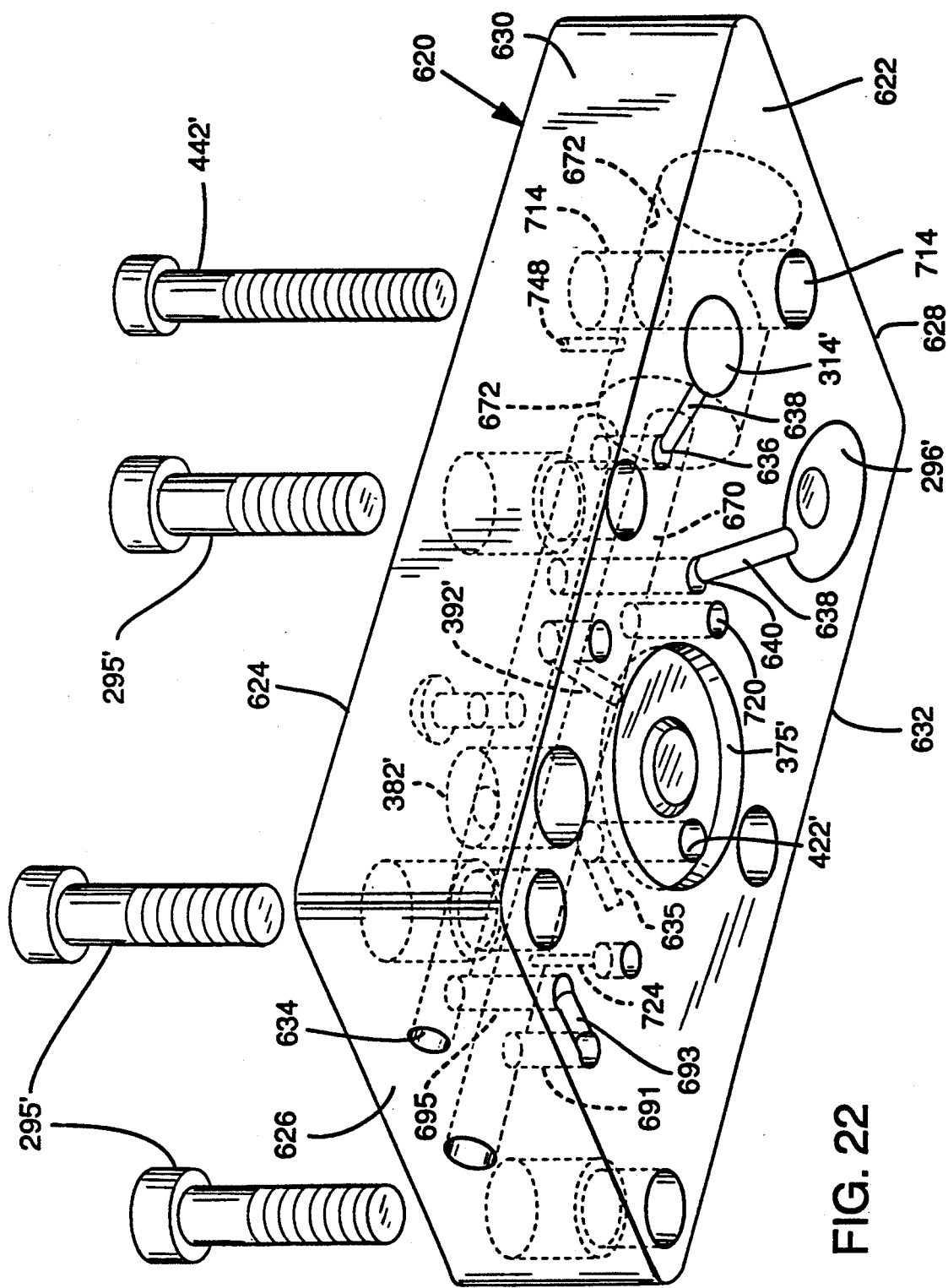
FIG. 22 is a perspective view of the control block utilized in the modification of FIG. 21.
Figure 23:
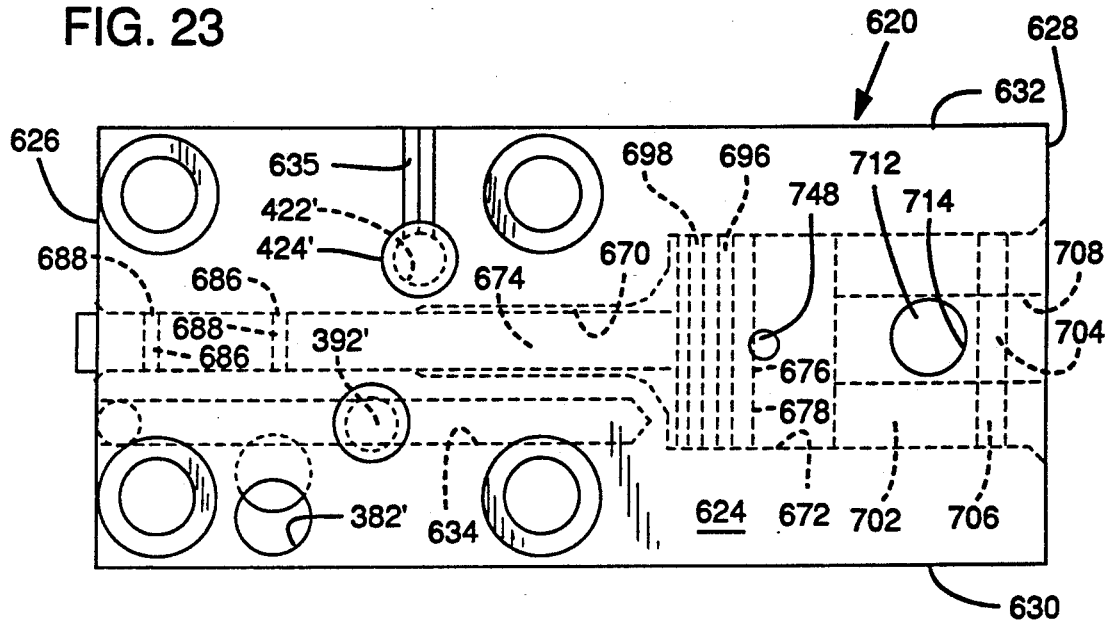
FIG. 23 is a top view of the control block of FIG. 22.
Figure 24:
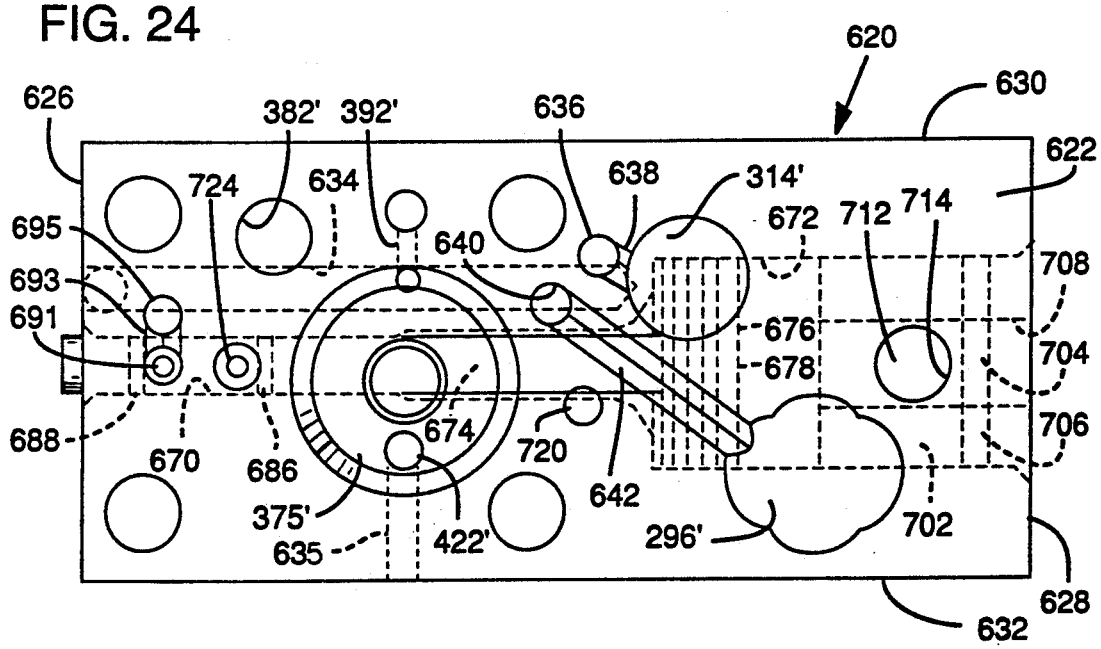
FIG. 24 is a bottom view of the control block of FIG. 22.

Referring to FIGS. 22, 23 and 24, the cap 620 has a bottom surface 622, a top surface 624, opposite end surfaces 626, 628, and opposite side surfaces 630, 632. The cap 620 is adapted to be secured by a plurality of fastening screws 295' and 442' to the control block 154 in the same manner as the cap 158 and has many other features in common to the cap 158, including a recess 375' and hold back recesses 296', 314' and 382' in the bottom surface.

The cap 620 also has a passage 392' connecting with the passage 390 in the control block 154 to convey holdback air to the chamber or recess 375'.

Extending inwardly from the end surface 626, is a passageway 634 which intersects the recess 382' which is formed by drilling upwardly from the bottom surface 622. It also intersects a passage 636, also formed by drilling from the bottom surface 622. A grove 638 is formed in the bottom surface 622 between the passageway 636 and the recess 314'. Also intersecting the passage 634 is a passage 640 drilled from the bottom surface 622. A groove 642 in the bottom surface intersects the opening 640 and the recess 296'. A bleed-off opening 422' to the recess 375' is also provided the opening being closed by a screw 424'. The top surface 628 has a groove 635 therein that functions to form a bleed-off air channel when a further attachment to be described is secured to the top of the block 620. The end of the passageway 634 is closed by a pressed-in seal 642.

The cap 620 is provided with a piston receiving cylinder including a stem receiving bore 670 formed therein and a piston head receiving counter bore 672. Slidably mounted within the bore 670 is the stem 674 of a piston 676 having an enlarged head 678 adapted to slide within the counter bore 672. The stem 674 is provided with a pair of longitudinally spaced annular grooves 682, 684 in which are received o-rings 686, 688, respectively.

The head 678 is likewise provided with a pair of longitudinally spaced annular grooves 692, 694, in which are received lip or U-cup seals 696, 698, respectively. The lip seal 696 is one effective to prevent the flow of air in the direction from the top of the head forward to the stem, while the lip seal 698 is one effective to prevent air flow in the opposite direction. In the outer end of the counter bore 672 is an end cap 702 having a groove 704 receiving an o-ring 706 that frictionally engages the sidewalls of the counter bore 672 to retain the end cap in place and form an air seal therearound. The end cap 702 has a central bore 708 which is internally threaded adjacent the outer end of the cap to receive a cooperatively threaded barb to which may be connected the hose 568' (see FIG. 25) connected to the normally open valve in the handpiece hanger 30. The end cap 702 is bored diametrically to provide an opening 712 therethrough in line with the opening 714 in cap 620 and opening 444 in control block 154. The screw 442' extends through holes 714 and 712 and into the opening 444 in the control block 154 whereby air may pass from the bleeder valve 448 into the bore 708. A further opening 720 is provided in the valve body from the bottom face 622 into the bore 670 adjacent its end near the counter bore 674. The opening 720 communicates with a passage 721 in the block 154 which extends upwardly from a through passage 722 (see FIG. 7) which communicates with the slot 208 in the manifold 152. The manifold opening 204 with which the slot 208 communicates, is adapted to receive a barb (not shown) having a 0.005" bleed orifice built therein and which is supplied from the 30 psi air source by a suitable line (not shown). The diaphragm 160 has an opening 723 in line with the openings 720 and 721.

Figure 25:
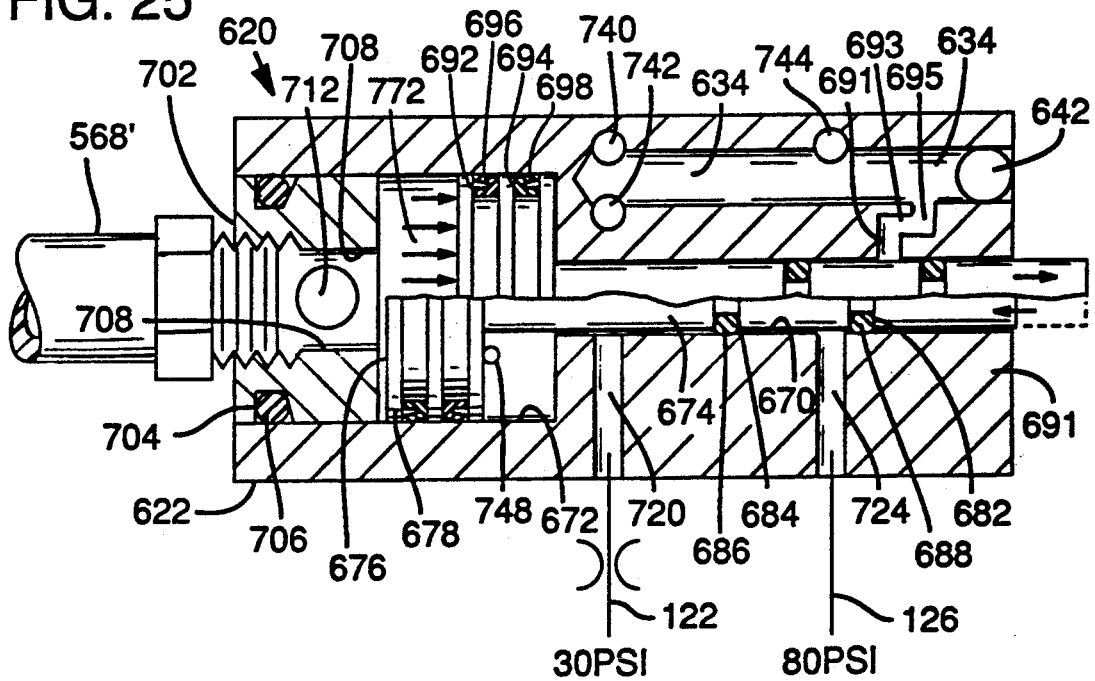
FIG. 25 is a schematic view of the control block of FIG. 22 illustrating in the top half of the view one position of the valve piston therein and in the bottom half of the view the other position of the valve piston therein.

Another opening 724 is provided through the valve body 668 from the bottom face 622 into the bore 670 between the o-rings 686, 688, such that it is between the o-rings 686, 688 in both positions of the valve head 678, as shown in FIG. 25. The opening 724 communicates with a passageway 727 in the control block 154 which extends upwardly from a passageway 728 extending through the block and communicating with the port 202 in the manifold 152. In operation, the port 202 is supplied with 80 psi air. The diaphragm 160 has an opening 730 in line with the passageway 727.

Communication is also provided from the bore 670 to the passageway 634 by means of a passage 691 extending from the bore 670 to the face 622 of the cap 620 which has a groove 693 therein communicating with a passageway 695 which extends into the passageway 634. The passageway 691 is positioned so that it opens into the bore 670 on the opposite side of the o-ring 688 from the opening 724 when the valve head is to the left position shown in FIG. 25 closely adjacent the cap 102, but is between the o-rings 686, 688 when the valve head is in its right position remote from the end cap 702, as shown in FIG. 25.

The operation of the valves 660, 662 and 664 will now be described, first with reference to the upper portion of FIG. 25, wherein the valve is shown in the position it assumes when a handpiece 20 is in its hanger 30, which will close off the tubing 568'. As a result of this closure, 80 psi air entering through the opening 714 will build up between the end cap 702 and the piston head 678 overcoming the 30 psi pressure on the underside of the head and causing the piston 676 to shift to the right to the position shown in the upper part of FIG. 25. This will effect an opening between the passages 691 and 724 allowing 80 psi air to pass into the passageway 634. This pressure will be applied to the diaphragm above the recesses 296', 314', 375' and 382' closing off all flow of fluid through the control block for such handpiece.

Figure 21:
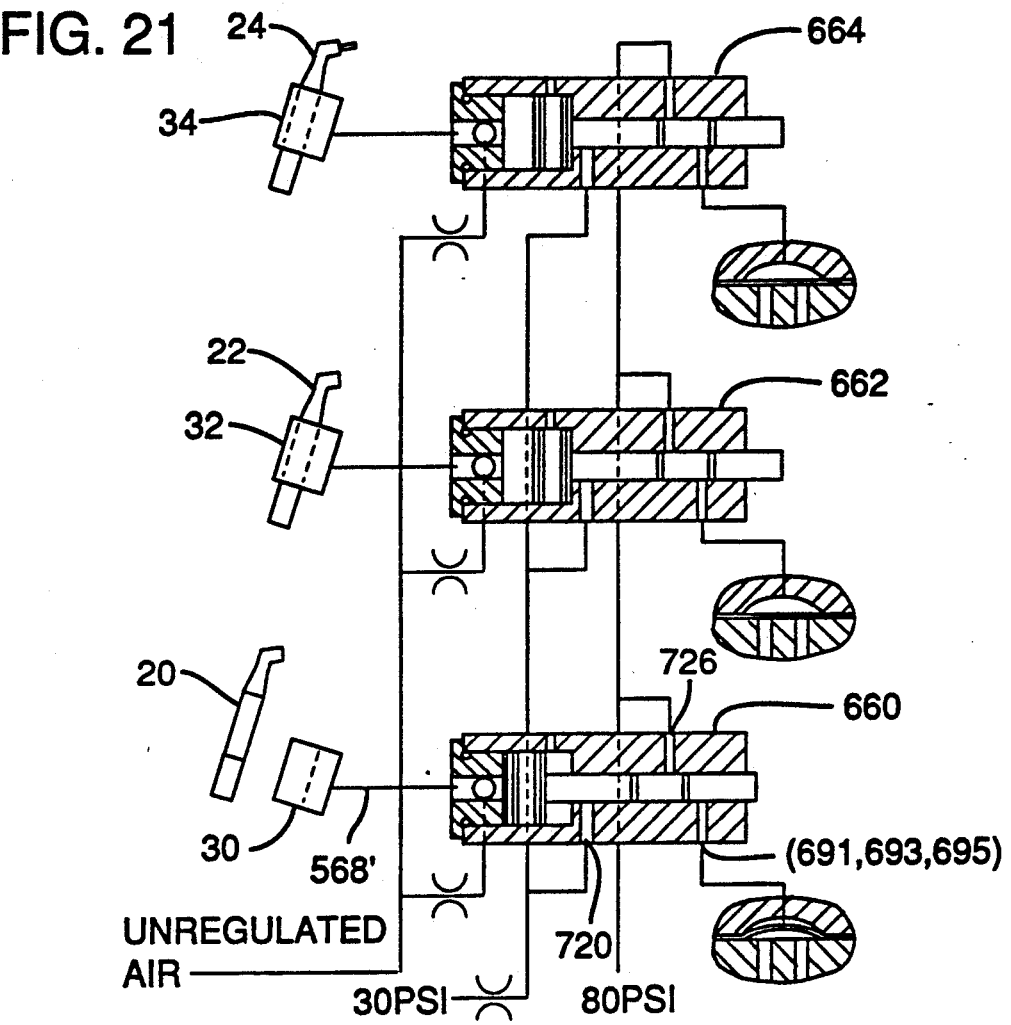
FIG. 21 is a schematic flow diagram of a modification of the invention which will cut off flow to all other handpieces upon lifting of one handpiece from its hanger.

Referring to FIG. 21 and the lower portion of FIG. 25, if the handpiece 20 is lifted from its hanger 30, the hanger valve will open allowing air to vent from the counterbore 672 through the end cap 702 reducing to atmospheric pressure the pressure on the left side of the head 678. Since the right side of the head 678 is subjected to 30 psi by reason of he 30 psi air passing into the valve through the opening 720, the valve 676 will shift to the left. This 30 psi air is restricted by a 0.005 barb threaded into port 204 of manifold 152. A vent opening 748 is provided from the top surface 628' into the counter bore 672 such that it becomes exposed after the head 678 has shifted the left sufficiently to close off the flow between the passage 724 and the passage 691 and vent the three holdbacks through the stem bore 670. The exposed port 748 will vent the air pressure underneath the head 676 so that movement of the head stops. Through the passages 720 in each valve and the passages 721, 722 in the control blocks 154 the underside of the pistons of the units 662 and 664 will be vented to open and they will not shift position even if the handpieces 22 and 24 are lifted.

The control apparatus is also designed to accommodate an electrical switch for activating an electrical circuit to the lamp in a fiber optic system if the same is incorporated in the handpiece. Referring to FIGS. 26, 27 and 28, such a switch, indicated at 800, is adapted to be mounted on the top of the control cap 158 or the control cap 650. In the instance of the mounting on the control cap 158, the switch will be mounted upon the flat 804 formed on the cap 158 and secured thereto by means of two fastening screws including the vent screw 424 and a screw 806 extending through cooperative openings in the switch 800. The screw 424 engages in the opening 422, the screw 806 engages in a threaded opening 808 provided in the cap 158, see FIG. 3. The openings 808, 422 straddle an opening 810 which extends from the top of the cap 158 into the passageway 294. The opening 810 is closed by a suitable washer and screw 812, as shown in FIG. 3, when the switch 800 is not incorporated into the apparatus. The switch 800 comprises a generally rectangular top plate 802 formed of non-conductive material. The top plate 802 is formed with a hat-shaped recess 814 positioned over the opening 810 and defining a downwardly facing annular shoulder 816. Secured to the underside of the top plate 802 is a circuit board 818 formed of insulating material and having a central opening 820 concentric with the recess 814 and having a diameter no greater than about the inner diameter of the shoulder 816. Secured to the upper surface of the circuit board 818 is a pair of conductor elements 822, 824 having facing semi-annular end portions concentric with the opening 820. Secured to the lower surface of the circuit board 818 is a spacer board 826 having a stepped opening 828 concentric with the circuit board opening 820 and defining an annular downwardly facing shoulder 830. Clamped thereby in sealing relation to the cap surface 804 is a hat-shaped elastomeric diaphragm 832 positioned in the openings 820, 828 with the rim 834 thereof extending under and clamped by shoulder 830. Positioned in the lower part of the recess 814 beneath the shoulder 816 is a cup-shaped connector element 836 formed of conductive material. Positioned above the connector element 836 is a coil spring 838 which biases the connector element downwardly towards the conductor elements 822, 824. When the passageway 294 is vented to atmosphere, the spring 838 forces the connector element 836 into contact with the conductor elements 822, 824. However, when the handpiece is in its hanger, the pressure within the passageway 294 against the diaphragm 832 forces it upwardly so as to move the connector element 836 out of contact with the conductor elements 822, 824 to open the circuit between them. Also secured to the upper surface of the circuit board is a further conductor element 840 which is positioned so as not to be contacted by the connector element 836.

The switches 800 are provided with a pair of connector pins 842 extending from one side thereof and a pair of sockets 844 on the opposite side so that switches on adjacent blocks may be connected together. Also, a pair of connector pins 846 are provided for connection to the socket connector 848 of leads connected to the light source of the handpiece.

FIG. 29 is a schematic diagram of the electrical circuit in the switches 800 supplied from a suitable source of electrical power through a male connector 850 which can be plugged into the sockets 844 on one of a series of switches 800. The switches are each provided with parallel leads 852, 854 extending from the sockets 844 on one side to the pins 842 on the other. The connector element 822 of each switch is connected to the lead 852, while the connector element 824 is connected to one of the connector pins 846 of the switch. The connector element 840 is connected between the lead 854 and the other of the connector pins 846.

Having illustrated and described various embodiments of the invention it will be apparent the invention permits of modification in arrangement and detail. We claim all such modifications as come within the scope and purview of the appended claims.

We claim:

1. A control system for controlling the supply of air and water to a plurality of dental handpieces and the like comprising:

a plurality of control blocks each having an upper face, a pair of opposed side faces, and a bottom face;

said control blocks arranged side by side in a row;

a manifold block positioned at one end of said row and a closure block at the at the other end of said row, said manifold block having a pair of parallel faces, one of which faces the adjacent control block;

a plurality of inlet means in said manifold block and a plurality of passages in said manifold block extending therethrough to outlets in said one face thereof;

a plurality of fluid passages through said control blocks having entrance ports in registry with the fluid outlets of said manifold block;

a plurality of outlets in each of said control blocks;

a plurality of valve means in each of said control blocks;

each said valve means comprising an integral cartridge valve member removably mounted in said control blocks and removable through the bottom surface thereof; and passageways in said control blocks for conveying fluid from said manifold block to said valve means and from said valve means to certain of said control block outlets.

2. A control block for a control system for controlling the supply of water to a dental handpiece:

said control block having a plurality of faces and having an inlet in a first face thereof for the admission of water and an outlet in a second face thereof for the discharge of water;

passageway means in said control block connecting said inlet to said outlet;

an on/off flow control valve means in said passageway means for controlling the flow of water from said inlet to said outlet; and said on/off flow control valve means comprising an integral cartridge valve member including a housing having a hollow stem, an inlet opening in said stem for conveying water from said passageway means into said stem and an outlet opening in said stem for conveying water from said stem into said passageway means, a movable valve core in said stem and cooperative seat means on said core and the inner wall of said stem for controlling flow of water from said inlet opening to said outlet opening;

said cartridge valve member housing being removably mounted in said control block and removable through a face of said control block whereby said valve member can be easily removed from said control block and replaced with a similar cartridge valve member in the event of a malfunction of any component thereof.

3. A control block as set forth in claim 2 comprising an adjustable valve means operatively arranged with said passageway means between said inlet and said outlet for controlling the rate of flow of water from said inlet to said on/off flow control valve.

4. A control block as set forth in claim 2 wherein flush water means are provided for introducing flush water into the said passageway means between said on/off flow control valve means and said outlet:

said flush water means comprising an integral cartridge valve member mounted in said control block including a valve body having an inlet and an outlet;

a check valve means mounted in said valve body to permit flow only from said valve body inlet to said valve body outlet;

an inlet for flush water in said control block first face;

a first passageway in said control block connecting said flush water inlet to said valve body inlet; and a second passageway in said control block connecting said valve body outlet to said passageway means between said on/off flow control valve means and said outlet in said second face.

5. A control system as set forth in claim 4 wherein said check valve means is a duckbill valve.

6. The control system of claim 2 including a manually operable valve between said inlet and said on/off flow control valve means for controlling the rate of flow of water to said on/off flow control valve.

7. The control block of claim 2, wherein said control block comprises a top and a bottom face:

said cartridge valve member being mounted in a cooperatively formed aperture extending through said block from said bottom face to said top face; and said cartridge valve member being removable through said bottom face.

8. The control block of claim 7 comprising:

a valve stem in said valve member movable between a downward valve open position and an upward valve closed position;

a spring in said valve member operatively arranged with said valve stem biasing the same toward said closed position;

a valve operating cap in operative engagement with said stem positioned in said aperture above said core;

a flexible diaphragm extending across the top face of said body;

a diaphragm holddown block mounted on said control block over said diaphragm;

said diaphragm holddown block having a recess therein positioned over said cap whereby said cap may deform said diaphragm and protrude into said recess;

a first air inlet into said recess above said cap for admitting air under pressure sufficient to create a force to depress said diaphragm, said cap and said valve stem; and a vent means communicating with said recess above said diaphragm to vent air therein at a rate substantially slower than air is admitted thereto through said first air inlet.

9. The control block of claim 8 including:

spring means in operative engagement with said cap for biasing the same upwardly so that it protrudes above said top face.

10. In a control system for dental handpieces, the combination comprising:

a control block;

said control block having a plurality of faces and having an inlet in a first face thereof for the admission of water and an outlet in a second face thereof for the discharge of water;

passageway means in said control block connecting said inlet to said outlet;

an on/off flow control valve means in said passageway means for controlling the flow of water from said inlet to said outlet;

said on/off flow control valve means comprising an integral cartridge valve member removably mounted in said control block and removable through a face of said control block;

flush water means comprising an integral cartridge valve member mounted in said control block including a valve body having an inlet and an outlet;

a check valve means mounted in said valve body to permit flow only from said valve body inlet to said valve body outlet;

an inlet for flush water in said control block first face;

a first passageway in said control block connecting said flush water inlet to said valve body inlet;

a second passageway in said control block connecting said valve body outlet to said passageway means between said on/off flow control valve means and said outlet in said second face;

a source of flush water;

conduit means connecting said source of flush water to said inlet; and an off/on valve means in said conduit means for controlling the flow of water to said inlet.

11. In a control system for a dental handpiece having an air inlet for both coolant air and chip air:

a control block having a coolant air passageway extending between a first inlet in a face thereof to a first port in a second face thereof;

means for connecting said first inlet to a source of low-pressure air;

a chip-air passageway in said control block extending from a second inlet in a face thereof to a second part in said second face adjacent to said first port;

high-pressure air means for connecting said second inlet to a source of high-pressure air;

an outlet port in said control block second face adjacent to said first and second ports;

an outlet passageway extending between said outlet port and an outlet in a face of said block;

a dental handpiece;

first conduit means connecting said outlet to said dental handpiece;

a flexible diaphragm positioned on said first face across said ports;

a diaphragm holddown block mounted on said control block over said diaphragm and having a recess therein over said ports;

air supply means for supplying air under a pressure intermediate said low-pressure air and said high-pressure air to said recess above said diaphragm at a predetermined rate;

hanger means for releasably supporting a dental handpiece;

normally upon valve means in said hanger means adapted to be moved to closed position when the handpiece is positioned in said hanger means, the outlet of said hanger valve means being open to atmosphere;

second conduit means connecting said recess to said hanger valve means whereby when said hanger valve means is closed air bleeding into said recess through said air supply means will depress said diaphragm to close said ports, and when said hanger valve means is open said air in said recess will vent to atmosphere thereby permitting said low-pressure coolant air to lift said diaphragm and to flow from said fist port to said outlet port; and manually operable valve means in said high-pressure air means for controlling the passage of high-pressure air to said second inlet whereby when said high-pressure air is admitted to said second inlet said diaphragm is displaced to permit flow of air from said second port to said outlet port and thence to said dental handpiece thereby to provide a supply of chip air to said dental handpiece.

12. The control system of claim 11 including a manually controlled valve for controlling the rate of flow of air to said first inlet.

13. The control system of claim 12 wherein said air supply valve means comprises an integral cartridge valve removably mounted in said control block and removable through a face thereof.

14. In a control system for a dental handpiece having a fiber optic light source therein, said control system including a control block assembly comprising pneumatically controlled valve means for controlling the flow of air and water to said handpiece, said pneumatically controlled valve means including:

a hanger means for said handpiece, a normally open valve in said hanger means adapted to be closed upon positioning of said handpiece in said hanger means, and a chamber in said control block assembly adapted to be vented to atmosphere when said hanger valve is open and means for supplying air under pressure to said chamber when said hanger valve is closed, the improvement comprising a switch means for said light source comprising a switch body mounted on said control block assembly;

a diaphragm positioned between said control block assembly and said switch body;

an opening in said control block assembly beneath said diaphragm communicating with said chamber;

a pair of spaced-apart electrical contacts positioned above said diaphragm;

a contact element positioned above said electrical contacts movable toward and away therefrom;

spring means in said switch body biasing said contact element toward said electrical contacts; and electrical circuit means for connecting said electrical contacts to a source of electrical power and to said light source;

whereby when said handpiece is in said hanger means air pressure in said chamber will cause said diaphragm to elevate said contact element and open the circuit to said light source, and when said handpiece is removed from said hanger means said spring means will move said contact element against said contacts to close the circuit to said light source.

15. In a control system as set forth in claim 14 comprising a plurality of said control block assemblies and switch means mounted side by side wherein said electrical circuit means comprises male connector means on a side edge of each of said switch bodies and female connector means of a next adjacent switch body for connecting said switch means to a source of electrical power.

* * * * *

UNITED STATES PATENT AND TRADEMARK OFFICE
CERTIFICATE OF CORRECTION

PATENT NO. : 5,201,899

DATED : April 13, 1993

INVENTOR(S) : Austin, Jr., et al.

It is certified that error appears in the above-identified patent and that said Letters Patent is hereby corrected as shown below:

Column 4, line 52, "th" should read --the--;

Column 5, lines 53 and 54, "openings simply" should read --openings--;

Column 11, line 14, "to from" should read --to--;

Column 14, line 44, "shifted the" should read --shifted to the--;

Column 16, claim 1, line 6, "at the at the" should read --at the--;

Column 17, claim 8, line 36, "body" should read --block--; and

UNITED STATES PATENT AND TRADEMARK OFFICE
CERTIFICATE OF CORRECTION

PATENT NO. : 5,201,899
DATED : April 13, 1993
INVENTOR(S) : Austin, Jr., et al.

It is certified that error appears in the above-indentified patent and that said Letters Patent is hereby corrected as shown below:

Column 18, claim 11, line 30, "part" should read --port--.

Signed and Sealed this

Twenty-fifth Day of January, 1994

Attest:

BRUCE LEHMAN

*Attesting Officer*     *Commissioner of Patents and Trademarks*